(12) United States Patent
Waxman

(10) Patent No.: US 11,478,545 B2
(45) Date of Patent: Oct. 25, 2022

(54) FHSS HOTSPOT DEVICE AND METHODS

(71) Applicant: Shai Waxman, Sunnyvale, CA (US)

(72) Inventor: Shai Waxman, Sunnyvale, CA (US)

(73) Assignee: Shai Waxman, Pebble Beach, CA (US)

( * ) Notice: Subject to any disclaimer, the term of this patent is extended or adjusted under 35 U.S.C. 154(b) by 1094 days.

(21) Appl. No.: 16/321,466

(22) PCT Filed: Sep. 16, 2016

(86) PCT No.: PCT/IB2016/055560
§ 371 (c)(1),
(2) Date: Jan. 29, 2019

(87) PCT Pub. No.: WO2017/144962
PCT Pub. Date: Aug. 31, 2017

(65) Prior Publication Data
US 2019/0273531 A1 Sep. 5, 2019

Related U.S. Application Data

(60) Provisional application No. 62/300,850, filed on Feb. 28, 2016.

(51) Int. Cl.
*H04B 1/715* (2011.01)
*A61K 39/35* (2006.01)
(Continued)

(52) U.S. Cl.
CPC .............. *A61K 39/35* (2013.01); *A61K 31/58* (2013.01); *A61K 38/164* (2013.01); *A61P 37/08* (2018.01);
(Continued)

(58) Field of Classification Search
CPC ............. H04B 1/715; H04B 1/04; H04B 1/16
See application file for complete search history.

(56) References Cited

U.S. PATENT DOCUMENTS

| 2004/0146121 A1* | 7/2004 | Brown | H04B 1/30 375/322 |
|---|---|---|---|
| 2007/0047669 A1* | 3/2007 | Mak | H04B 1/28 375/316 |
| 2008/0159442 A1* | 7/2008 | Tanabe | H04L 27/3863 375/324 |

* cited by examiner

Primary Examiner — Zhiren Qin

(57) ABSTRACT

A wireless wideband transceiver may be able to communicate with multiple frequency-hopped spread-spectrum (FHSS) devices concurrently over multiple frequencies over a short range by including a plurality of digital chains corresponding to the FHSS physical channels, individually and dynamically compensated for in-phase/quadrature imbalance in the transmit and/or receive portion. To further improve communications the transceiver may also mitigate cross interference between adjacent channel signals that are received and/or transmitted simultaneously, avoid false reception and/or transmission of co-channel signals, delay respective FHSS channels transmissions relative to other channels transmissions, speed up connection to FHSS devices and coordinate Time Division Duplexing (TDD) operation according to application dependent TX/RX binary pattern. A device that includes such a transceiver (FHSS-hotspot) may enable the concurrent usage of multiple commercially available FHSS peripheral devices without the need for additional personal host devices to be carried along with them, and in addition enable the concurrent usage of multiple commercially available FHSS personal data devices while reducing their radiation and/or latency and/or usage cost and/or power, to establish a localized multi-device multimedia session, and/or to interface with a communications network to communicate with remote parties, and/or to interface with broadcast devices to stream contents.

13 Claims, 21 Drawing Sheets

(51) Int. Cl.
   *A61P 37/08*      (2006.01)
   *A61K 31/58*      (2006.01)
   *A61K 38/16*      (2006.01)
   *C12N 15/117*     (2010.01)
   *H04B 1/04*       (2006.01)
   *H04B 1/16*       (2006.01)
   *H04B 1/7156*     (2011.01)
   *H04B 1/40*       (2015.01)
   *H04B 1/713*      (2011.01)
   *A61K 39/00*      (2006.01)

(52) U.S. Cl.
   CPC .............. *C12N 15/117* (2013.01); *H04B 1/04* (2013.01); *H04B 1/16* (2013.01); *H04B 1/40* (2013.01); *H04B 1/713* (2013.01); *H04B 1/715* (2013.01); *H04B 1/7156* (2013.01); *A61K 2039/55561* (2013.01); *C12N 2310/315* (2013.01)

Classic Voice conference call setup

T_POLICY = TeSCO

Low energy Voice conference call setup

Advertising packet received during a scan slot anchor point set to Hotspot's fixed anchor point and connection request sent

· · ·

Fixed anchor point / 154' / 155'

153'

$T_{POLICY}$ = connInterval

Legend:
- Advertising
- Connect_Req
- Hotspot Data
- Users response

Slot_index=1..24 (~7.5msec)

Hotspot channel_index=1..Nch, Nch<=16

FHSS HOTSPOT DEVICE AND METHODS

TECHNICAL FIELD

Various aspects of this disclosure may pertain to wireless communications and, more particularly, to communications using Frequency-Hopped Spread-Spectrum (FHSS), and more particularly, to communications using FHSS devices that can communicate with multiple devices in FHSS multiple-access (FHSS-MA) system.

BACKGROUND ART

FHSS is the most commonly used technique for wirelessly connecting peripheral devices (e.g. headsets, speakers, controllers and mice) to their personal host device (e.g. Smartphone, tablet and laptop) over relatively short range (known as the Wireless Personal Area Network (WPAN) range i.e. <10 m). The majority of standard wireless communications devices using FHSS have low power consumption and are low cost, low latency and low radiation devices. The best known FHSS based standard is the 802.15.1 WPAN (Bluetooth®) standard.

In contrast to the wide adoption of the FHSS technique by short range personal wireless communications devices, the FHSS technique for longer range (known as the Wireless Local Area Network (WLAN) range i.e. <100 m) multi-user wireless communications was entirely replaced around the turn of the millennium by Orthogonal Frequency-Division Multiplexing (OFDM) technique and other techniques, to deliver higher data throughputs at the expense of higher power consumption, higher cost, higher latency and higher radiation, to date.

It may, therefore, be desirable to develop a device that may be able to communicate with multiple commercially available low cost, low power, low latency and low radiation FHSS (e.g. Bluetooth®) devices concurrently over multiple frequencies (e.g. Bluetooth® channels) over a relatively short range (that varies between WPAN range and WLAN range, hereby defined as "Wireless Group Area Network (WGAN)" range), without violating transmissions regulations. Such a device ("FHSS-hotspot") may enable the concurrent usage of multiple commercially available FHSS peripheral devices without the need for additional personal host devices to be carried along with them, and in addition, reduce the radiation and/or latency and/or usage cost and/or power consumption of multiple other mobile devices located in its proximity (e.g. Smartphone, Tablet computer) that communicate with it using FHSS technique, compared to other wireless communications techniques (e.g. WLAN, cellular). The FHSS-hotspot device functionality may be integrated in mobile devices (e.g. Smartphone, Tablet computer, Headphone, Helmet) and stationary devices (e.g. wireless router/bridge, gaming console, TV, sound system).

DISCLOSURE OF THE INVENTION

Various aspects of this disclosure present devices and methods that may be used to facilitate such communications. In one aspect, a wireless "FHSS-hotspot" device may be provided that may permit concurrent multimedia (video, audio, voice and other data) communications over multiple frequencies (channels) of multiple FHSS peripheral devices (e.g. Bluetooth® devices such as headsets, speakers, mice, controllers communicating over multiple Bluetooth® physical channels) to allow them to establish a localized multi-device multimedia session (e.g. conference call session, gaming session, streaming session, recording session), and/or to interface with a communications network (e.g. Ethernet, WLAN and cellular) to communicate with remote parties, and/or to interface with a broadcast device (e.g. radio, TV, media player) to stream contents, without the need for additional personal host devices to be carried along with the peripheral devices.

The FHSS-hotspot device may further permit concurrent multimedia (video, audio, voice and other data) communications over multiple frequencies (channels) of multiple personal data devices (e.g. smart phones, tablet computers that support Bluetooth® communications) to allow them to establish a localized multi-device multimedia session (e.g. conference call session, gaming session, streaming session, recording session), and/or to interface with a communications network (e.g. Ethernet, WLAN and cellular) to communicate with remote parties, and/or to interface with a broadcast device (e.g. radio, TV, media player) to stream contents, while possibly lowering their power consumption and/or radiation and/or latency and/or usage costs compared to other forms of communications (e.g., Wi-Fi Direct®, WLAN, cellular).

For example, a Bluetooth® headset may be useful, in such a scenario, to join a teleconference call without being paired with the user's mobile device; instead, multiple such headsets may pair and communicate concurrently over multiple frequencies (Bluetooth® physical channels) with the FHSS-hotspot device, which may then blend their audio signals and connect the headsets to a wired or wireless network, which may facilitate, for example, Voice-over-Internet-Protocol (Voice-over-IP or VoIP) telephone call. Multiple other personal data devices (e.g. Smartphone) may also pair and communicate concurrently over multiple frequencies (Bluetooth® physical channels) with the FHSS-hotspot device to join the teleconference call.

The FHSS-hotspot device transmitter and receiver (transceiver), according to another aspect of this disclosure, may utilize wide-band analog baseband (e.g. amplifiers, filters, data converters) and RF circuitry and may share it with other co-located wideband devices (e.g. WLAN) to reduce device costs and enable simultaneous transmission and simultaneous reception of both devices. In order to mitigate possibly strong interference of devices that communicate over the same frequency band (e.g. WLAN, WPAN, DECT and microwave devices) resulting from in-phase (I) and quadrature (Q) signals imbalance in the wideband transceiver, and in order to comply with transmissions standards/regulations, a dynamic frequency selective balancing technique for the in-phase (I) and quadrature (Q) signals may be implemented digitally.

The FHSS-hotspot device transceiver, according to another aspect of this disclosure, may disable reception and/or transmission of at least one of plurality of FHSS co-channel signals (i.e. FHSS signals sharing the same channel at the same time) for a limited period of time to avoid false reception (i.e. reception of co-channel data).

The FHSS-hotspot device receiver, according to another aspect of this disclosure, may mitigate cross interference between adjacent FHSS channel signals that are received simultaneously to increase the number of devices that may communicate reliably over a given frequency band, by performing parametric estimation of at least one interfering FHSS signal, regenerating the FHSS interfering signal(s) using its estimated parameters, up/down converting the FHSS regenerated interfering signal(s) and subtracting the resulting signal from the received signal to receive a desired FHSS channel signal.

The FHSS-hotspot device transmitter, according to another aspect of this disclosure, may mitigate cross interference between adjacent FHSS channel signals that are transmitted simultaneously to increase the number of devices that may communicate reliably over a given frequency band, by increasing the minimal frequency separation between adjacent FHSS channel signals that are transmitted simultaneously.

The FHSS-hotspot device transmitter, according to another aspect of this disclosure, may delay respective FHSS channel signal's transmission relative to a scheduled transmit instant, to be able to receive the response of the corresponding FHSS receiving device, and/or to minimize cross channel interference, and/or to avoid violating transmission standards/regulations.

The FHSS-hotspot device link controller, according to another aspect of this disclosure, may speedup FHSS connection establishment, by periodically signaling (controlling communications) over multiple frequencies (FHSS channels) simultaneously, and/or scanning for signaling over multiple frequencies (FHSS channels) simultaneously.

The FHSS-hotspot device, according to another aspect of this disclosure, may be able to avoid simultaneous transmission and reception of FHSS channels, by a-priori subdividing a periodic time interval allocated for data transmission to fixed time slots assigned for either transmission or reception of data according to a binary TX/RX pattern which is a function of the FHSS-hotspot's application, and scheduling its FHSS channels data transmissions and receptions according to that TX/RX pattern.

The FHSS-hotspot device, according to another aspect of this disclosure, may be able to reliably connect to additional FHSS devices during a session, by dividing time to fixed time intervals ("FHSS-hotspot Policy's time interval") which may further be subdivided to a first sub-interval that is assigned to periodic transmission or reception of data, and a second sub-interval that is assigned to none-periodic/one-time transmission or reception required to control communications e.g. establish connection (and/or assigned to a co-located device (e.g. WLAN) communications to allow concurrent communications of both devices).

The FHSS-hotspot device, according to another aspect of this disclosure, may use a single device address (e.g. Bluetooth® BD_ADDR) to be able to connect to FHSS devices that already established a bond with the FHSS-hotspot device (by storing each other's relevant parameters in a non-volatile memory) during its operation as a single FHSS channel device (e.g. Bluetooth® master device).

The FHSS-hotspot device, according to another aspect of this disclosure, may further mitigate cross interference between adjacent channel signals to increase the number of devices that may operate reliably over a given frequency band, by applying a multi-device power control technique that equalizes the average received power of its FHSS channels signals, and by equalizing the transmit power of its FHSS channels signals.

The FHSS-hotspot device, according to another aspect of this disclosure, may further mitigate audible ambient noise in its surrounding by proper blending of multiple FHSS devices' microphone signals that are concurrently received over multiple wireless synchronous connections.

The FHSS-hotspot device, according to another aspect of this disclosure, may continuously adapt the delay and volume of the audio streams of FHSS devices' speakers that are moving relative to it to control sound (e.g. acoustic beam forming, 3D sound), based on the FHSS-hotspot device's microphone input and/or the FHSS speakers' microphones inputs.

A FHSS device (including the FHSS-hotspot device), according to another aspect of this disclosure, may delay reconnection to a respective FHSS device that lost connection, to enable other FHSS device to connect to the respective FHSS device.

A FHSS device (including the FHSS-hotspot device), according to another aspect of this disclosure, may associate a short range FHSS device address (e.g. Bluetooth® device address) with a person, and try to contact the person by first trying to connect to the person's associated short range FHSS device (if it is discovered and if it supports the service required).

A FHSS device (including the FHSS-hotspot device), according to another aspect of this disclosure, may reduce electromagnetic-radiation when contacting a person, by first trying to connect to a trusted FHSS device in its proximity that supports the service required to contact that person (thus acting as a wireless bridge).

These and other aspects of the disclosure described below may be implemented alone and/or in various combinations. Furthermore, implementations of various devices and techniques may be in the form of hardware, software, firmware, etc., and/or combinations thereof.

BRIEF DESCRIPTION OF THE DRAWINGS

Various aspects of this disclosure will now be described in connection with the attached drawings, in which.

BEST MODE FOR CARRYING OUT THE INVENTION

Various aspects of the present disclosure are now described with reference to the accompanying drawing figures, it being appreciated that the figures may illustrate the subject matter of various embodiments and may not be to scale or to measure.

Figure 1A:
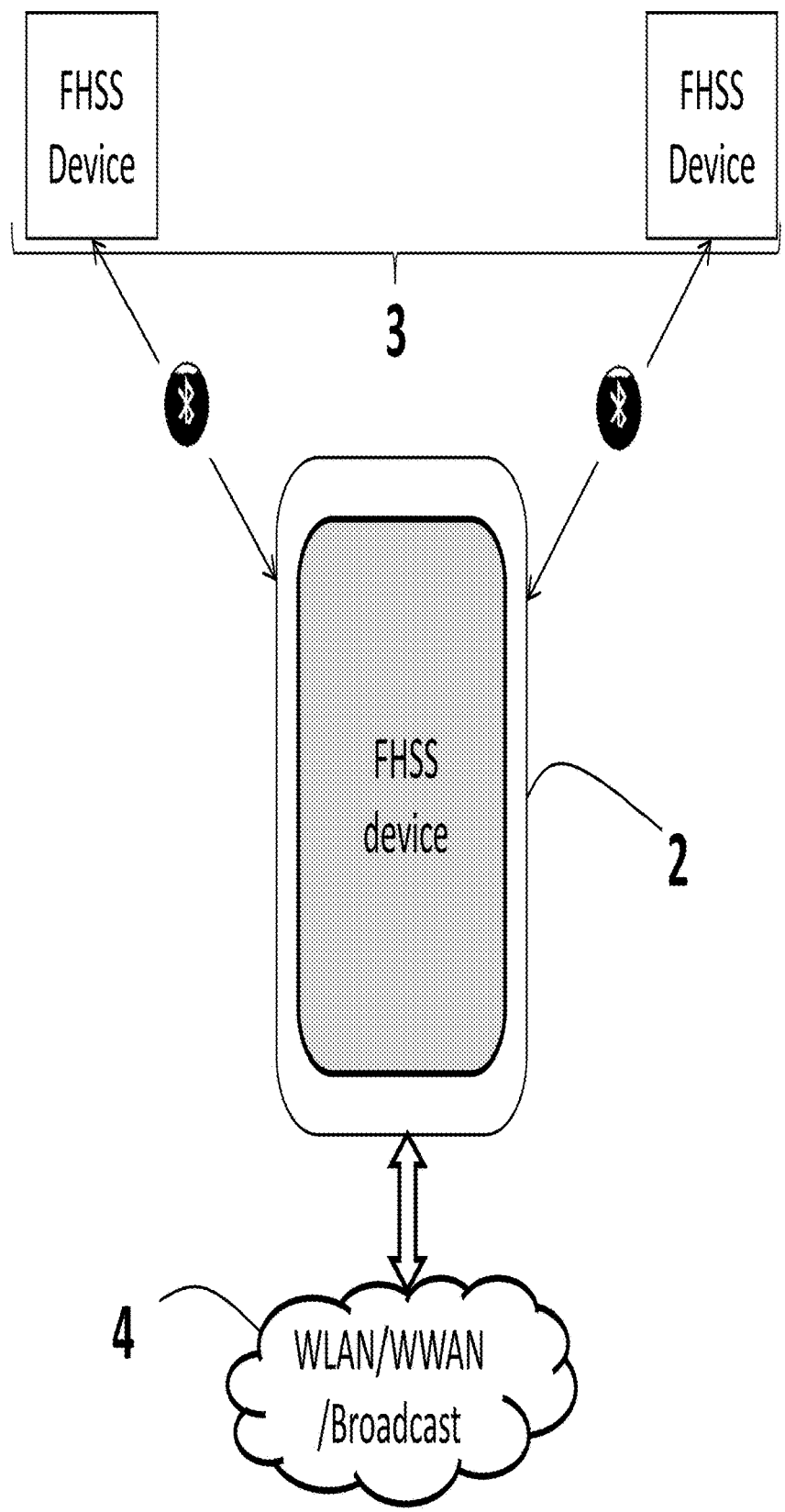
FIG. 1A shows a related system

FIG. 1A shows a standard Bluetooth® system configuration. A mobile telephone (which may be a Smartphone), tablet computer, or other personal device 2 may be wirelessly connected with one or more peripheral Bluetooth® standard devices 3, which may include, but are not limited to wireless headsets, wireless speakers, wireless keyboards or other input and/or output (I/O) devices. For example, according to the Bluetooth® specifications, the different devices 3 are "paired" with the device 2, in which the device 2 may be the master and the devices 3 may be slaves. The slave devices may communicate with the master using techniques that may be coordinated by the master device. Despite of the Bluetooth® protocol's ability to connect a master device to multiple slave devices, only two Bluetooth® slave devices may be able to concurrently communicate voice reliably, and only one Bluetooth® slave device may be able to stream audiovisual (AV) content from device 2 reliably, due to the Bluetooth® channel's limited bandwidth (capacity).

Figure 1B:
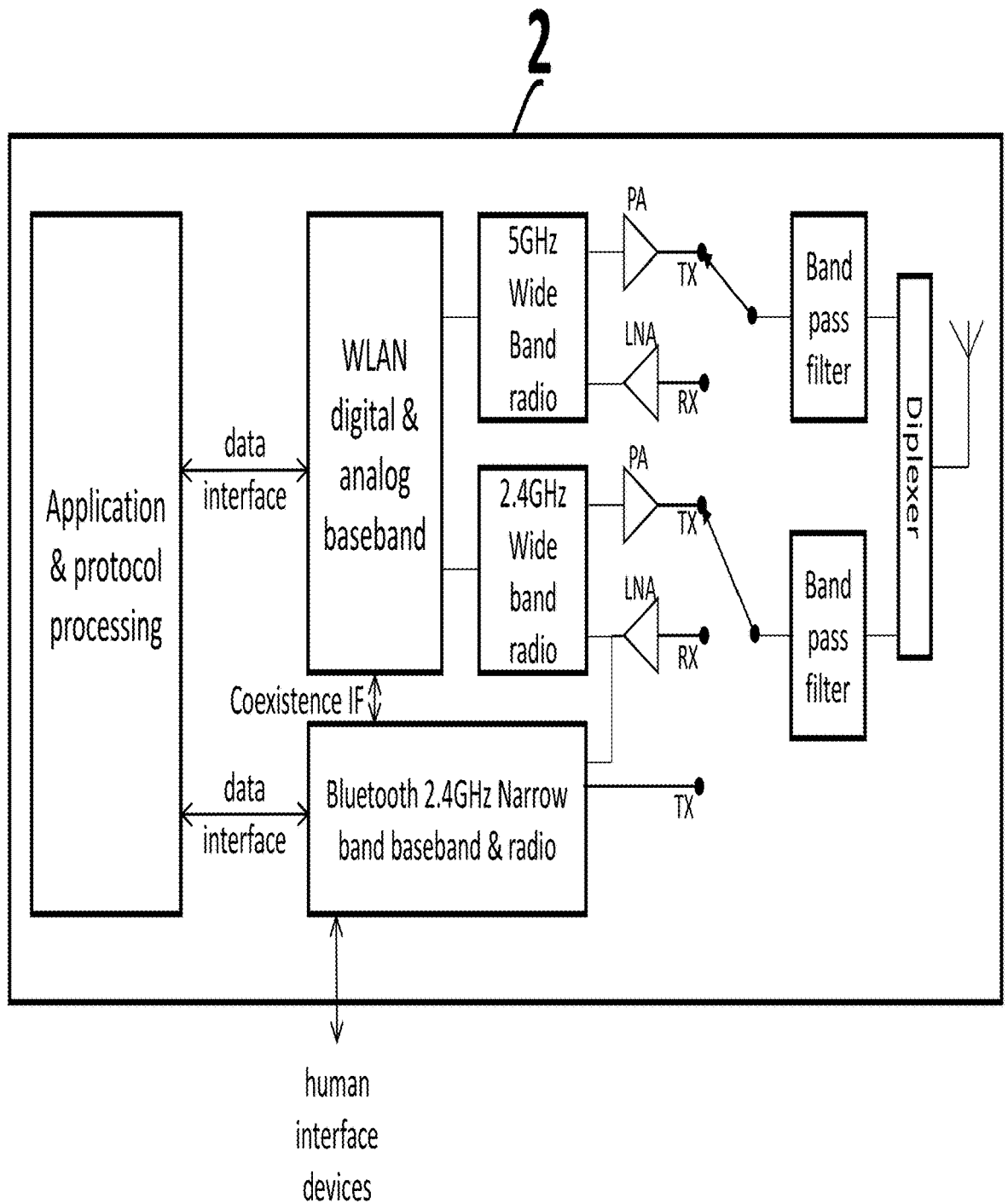
FIG. 1B shows a related device

FIG. 1B shows a conceptual diagram of a mobile device 2 that is able to communicate with Bluetooth® devices 3, and is also able to communicate with WLAN devices possibly concurrently by using various known coexistence techniques (e.g. time division, adaptive frequency hopping).

Figure 2A:
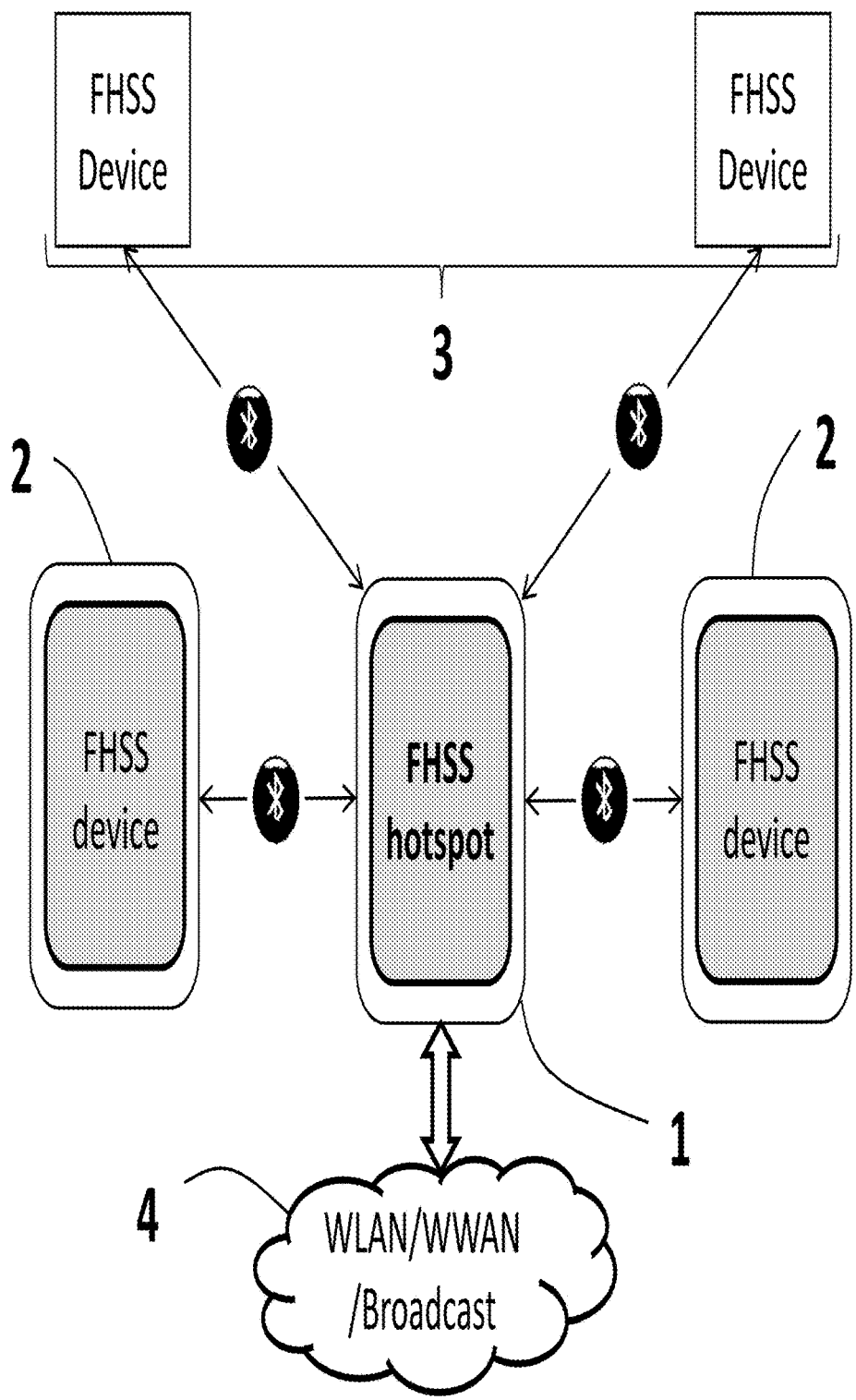
FIG. 2A shows a system in which various aspects of the disclosure may operate.

FIG. 2A shows a FHSS-MA system configuration according to an aspect of the disclosure. Multiple FHSS peripheral devices 3 (e.g. multiple Bluetooth® devices) which may have previously only been capable of communications through their personal device 2, as in FIG. 1A, may be wirelessly connected to the FHSS-hotspot device 1 and be able to simultaneously communicate all sorts of multimedia content (data, voice, audio and video) over multiple frequencies, and/or to interface with a broadcast device (e.g. radio, TV, media player) to stream contents, and/or establish a localized multi-device multimedia session (e.g. conference call session, gaming session, streaming session) without the need for additional personal host devices to be carried along with the peripheral devices. Such wireless connection may be performed in a manner similar to the pairing process in Bluetooth® networks; however, the invention is not thus limited, and other FHSS-MA protocols may be used. In a similar fashion, other personal FHSS devices such as, but not limited to, smartphones and tablet computers 2, may also be wirelessly connected to the FHSS-hotspot device 1. The FHSS-hotspot device 1 may provide connectivity to one or more WLANs and/or cellular networks 4, to permit the connected devices 2, 3 to communicate, e.g., with remotely-located devices. For example, the WLAN or cellular 4 may enable VoIP calling by means of the Internet or some other communication network, or other types of communication, which may include one-way and/or bi-directional multimedia communication.

Figure 2B:
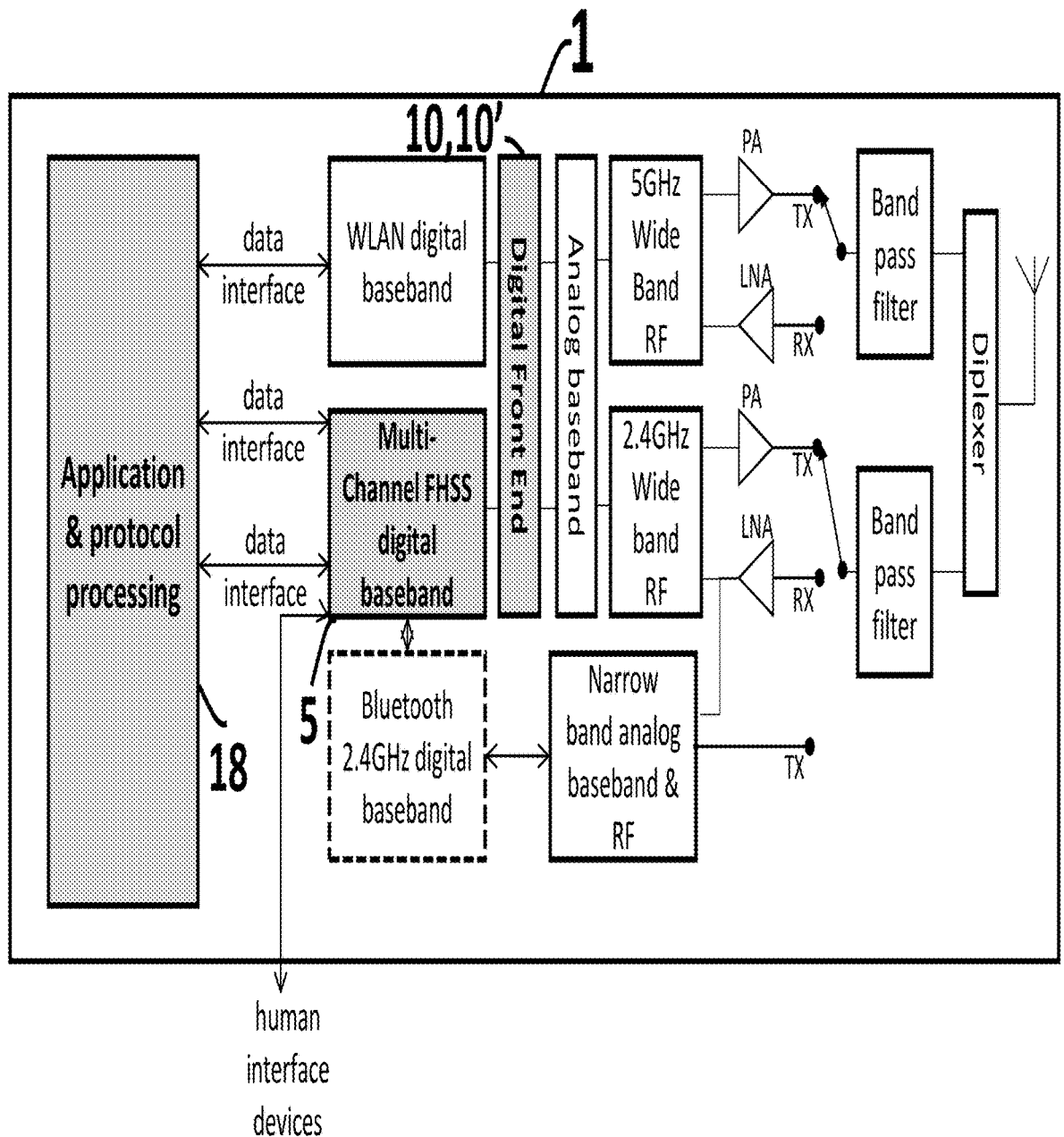
FIGS. 2B-2D show conceptual block diagrams of a FHSS-hotspot device in which various aspects of the disclosure may operate.
Figure 2C:
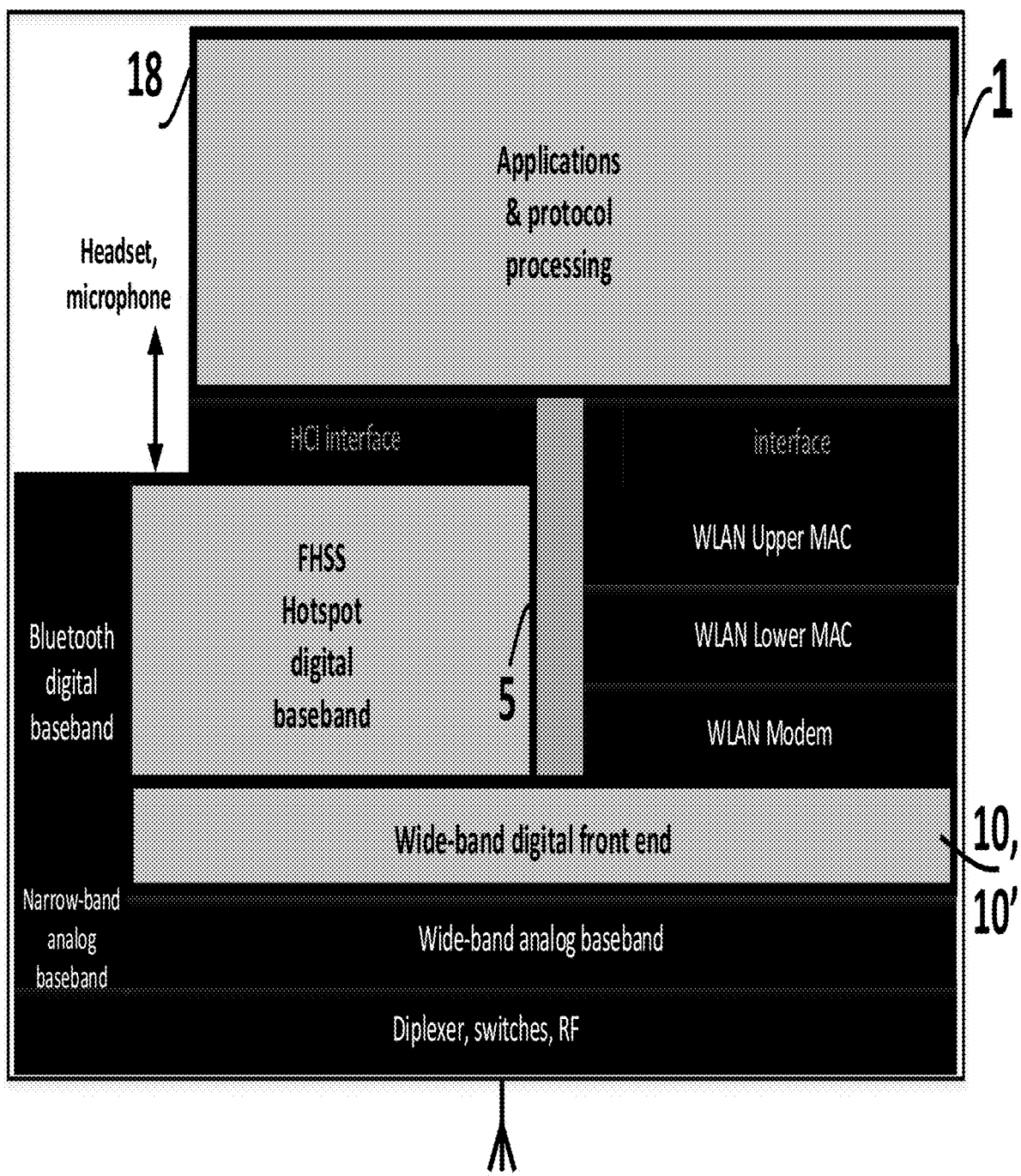

FIGS. 2B, 2C show conceptual diagrams of a FHSS-hotspot device 1. The device includes the FHSS-hotspot functionality according to various aspects of the disclosure (distributed across the highlighted multi-channel FHSS digital baseband circuitry 5, RX and TX wideband digital front end circuitry 10,10' and application and protocol processing 18), to communicate with multiple FHSS devices (e.g. Bluetooth® devices) all sorts of multimedia content (data, voice, audio and video) over multiple frequencies. Device 1 may also concurrently communicate with WLAN devices by using various known coexistence techniques (e.g. time division, adaptive frequency hopping). According to an aspect of this disclosure, the same wideband analog front end and RF may be used for both multi-channel FHSS and WLAN communications, which may require a balancing technique for the in-phase (I) and quadrature (Q) signals that may be implemented digitally in the RX and TX digital front ends 10,10'.

Figure 2D:
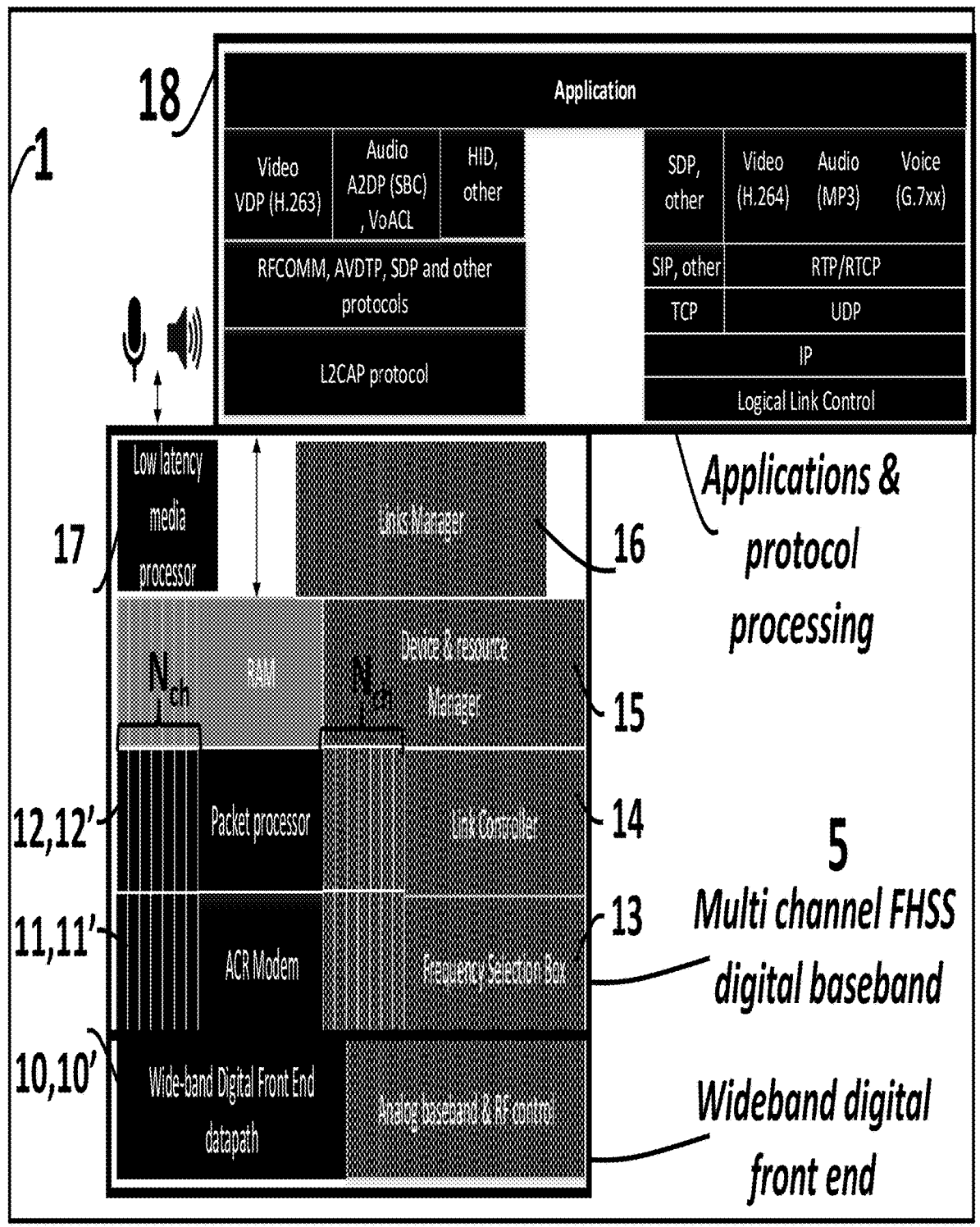

FIG. 2D shows a conceptual diagram of the FHSS-hotspot functionality included in device 1 including the data and control planes. The implementation of the FHSS-hotspot functionality will be explained further below, both with reference to FIG. 2D and other figures to be discussed.

Figure 3A:
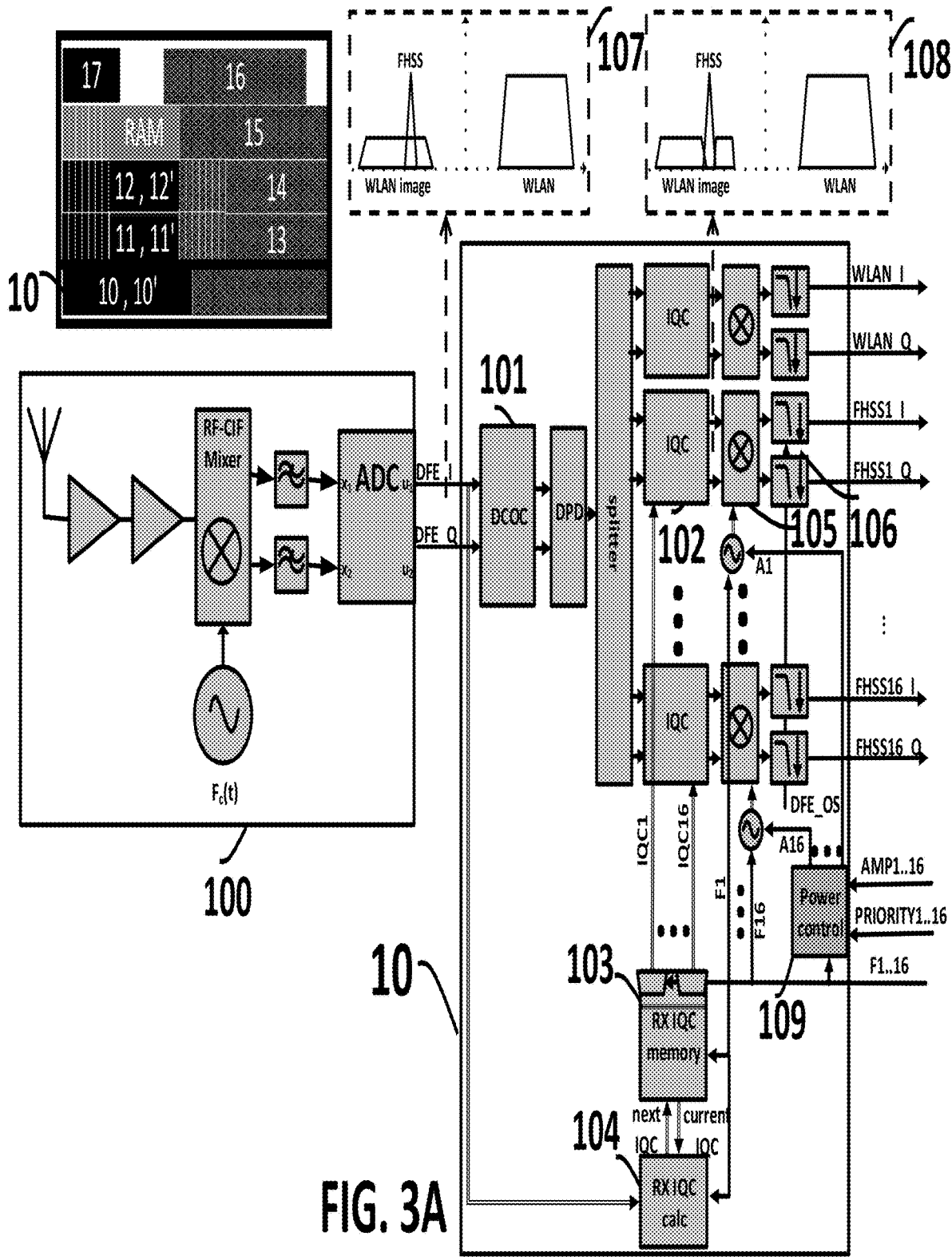
FIGS. 3A-3B show a conceptual block diagram of a FHSS-hotspot digital front end according to an aspect of the disclosure.
Figure 3B:
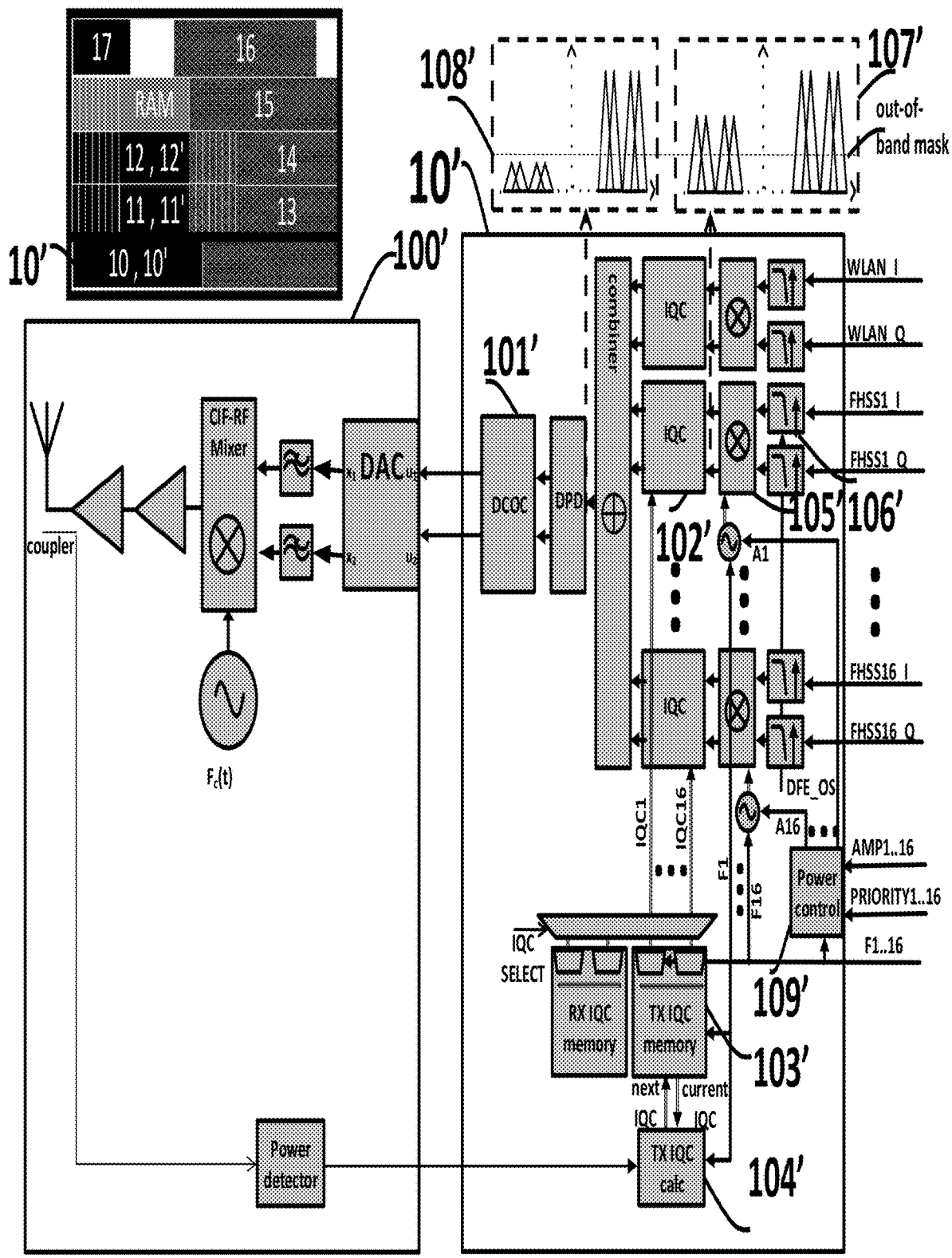

FIGS. 3A, 3B show an example of a transceiver that includes a digital front end that supports multi-channel FHSS (and WLAN) communications according to various aspects of the disclosure. FIG. 3A shows an example of a digital front end apparatus 10 in FIG. 2D of the receive side of the transceiver, while FIG. 3B shows an example of a digital front end apparatus 10' in FIG. 2D of the transmit side of the transceiver. It should be noted that by marking an apparatus numbering X by apostrophe (X') the text refers to the transmit apparatus corresponding to receive apparatus X It should be appreciated that apparatus 10 of FIG. 3A and apparatus 10' of FIG. 3B (or any pair of transmit and receive apparatuses with similar functionality for this matter) may be individual apparatus or may be combined and may share at least some components. For example, the antenna may be shared; a switch, circulator, duplexer or other multiplexing device (not shown) may then be inserted to share the antenna.

In FIG. 3A, a radio frequency (RF) signal may be received using a standard direct conversion wideband radio receiver architecture 100; the received signal may be filtered and amplified, using one or more amplification stages (two are shown, but there may be fewer or more stages). The result may be mixed in an RF-CIF mixer with a signal $F_c(t)$ generated by frequency generator to convert the RF signal to a complex intermediate frequency (CIF) signal having in-phase (I) and quadrature (Q) components, which may be low-pass filtered to retain the low-pass I and Q components. The low-pass I and Q signal components may then be input to an analog-to-digital converter (ADC) and converted to digital form and input to the receiver's digital front end 10. Values may be added to the digitized I and Q components by a direct-current offset cancellation (DCOC) circuit 101 also serving as local oscillator (LO) carrier leakage suppression circuit. Various direct-current/carrier offset cancellation techniques are known in the art, and the technique used here is not limited to any particular technique.

The digital I and Q output signals of the DC/carrier leakage suppression circuit 101 may be fed to digital post distortion (DPD) circuit followed by Nch (e.g. 16) parallel signal paths, corresponding to the Nch FHSS hopping sequences (physical channels). The Nch parallel signal paths will be described using the first parallel signal path, and it should be understood that the other signal paths may be substantially identical, except for various parameters (e.g., frequencies and coefficients).

In the first parallel signal path, the digital I and Q output signals of the DC/carrier leakage suppression circuit 101 (or DPD circuit if any) may be fed to I and Q inputs of an I/Q imbalance correction block 102. The I/Q imbalance correction block may receive a set of coefficients $IQC_1$ from a coefficient memory 103 (which may be a look-up table), where coefficients $IQC_1$ may be dynamically selected as a function of the first channel frequency hopping waveform frequency $F_1(t)$ (i.e. $IQC_1(t)=f(F_1(t))$ or simply $IQC_1=f(F_1)$). The coefficients $IQC_1=f(F_1)$ may be computed as needed, in a coefficients computation block 104 and stored in a memory address corresponding to frequency $F_1$. Note that block 104, whether a memory, look-up table, or computation block, may be a separate block for each parallel signal path or may be shared among two or more of the Nch parallel signal paths; in the form of a memory or look-up table, it may further be shared with coefficient memory 103. It is noted that multiple I/Q imbalance correction techniques are known in the art, and the inventive concept is not limited to any particular one of these techniques. Frequency selection box 13 in FIG. 2D may be used to generate $F_1$ or any other intermediate function of $F_1$ (e.g. using frequency indexes for memory access instead of actual frequencies) which may be fed to coefficient memory block 103 and coefficient computation block 104 and to a frequency generator that feeds a CIF-ZIF mixer 105. $F_1(t)$ may represent a particular digital hopping sine wave. The CIF-ZIF mixer 105 may receive the corrected I and Q signals from I/Q imbalance correction block 102 and may mix these signals with $F_1(t)$, which may be a digital hopping sine wave, to convert the CIF I and Q signals to near zero-intermediate frequency (ZIF) I and Q signals. The ZIF I and Q signals may then be low-pass filtered and decimated 106 and fed to a corresponding modem (denoted $FHSS_1$ for the first signal path), in which the resulting signals may be demodulated and data may be derived and sent to higher layers of the multi-channel FHSS digital baseband apparatus 5 and for further protocol and application processing 18 as shown in FIG. 2D.

A conceptual example of the I/Q imbalance correction is shown in boxes 107,108; in box 107 the power spectral density of the signal received from the radio 100 shows a strong WLAN signal received simultaneously with a weak FHSS signal. Due to the direct conversion radio I/Q paths imbalance the WLAN signal is interfering the FHSS signal's reception. Once the imbalance at the respective FHSS channel current frequency is corrected by I/Q imbalance correction block 102, the WLAN interference is attenuated as shown in box 108.

In FIG. 3A two or more frequency hopping waveforms frequencies $F_i(t)$, $F_j(t)$ may be identical due to the random nature of their selection (e.g. in Bluetooth® frequency hopping selection is pseudo-random). In such a scenario enabling the reception of incoming data from paths i and j may not be desirable to avoid false reception of a co-channel signal, and power control block 109 may disable reception on both paths or on a particular path (for example by controlling amplitude Ai and/or Aj of the corresponding receive paths) according to priority set by the device manager 15 shown in FIG. 2D (which may be based on comparative measure (e.g. power level, bit error rate, synchronous/non-synchronous data) between the paths).

The digital front end apparatus 10' of the transmit side of the transceiver, as shown in FIG. 3B, may operate in a similar fashion, but in reverse to the digital front end apparatus 10 of the receive side of the transceiver. In particular, digital ZIF I and Q signals from a modem (again, using the first parallel signal path of the transmit side for description purposes, this may be $FHSS_1$) may be interpolated and filtered 106', and the results may be fed to ZIF-CIF mixer 105', where they may be mixed with a digital frequency hopping waveform with frequency $F_1$ set by a frequency selection box 13 in FIG. 2D to generate CIF I and Q signals. The CIF I and Q signals may be fed to an I/Q imbalance correction block 102', where they may be corrected using a coefficient obtained from a coefficient memory (or generator, as discussed above) 103'. It is once again noted that multiple I/Q imbalance correction techniques are known in the art, and the inventive concept is not limited to any particular one of these techniques. The I signals and the Q signals from the Nch parallel signal paths may then be added, fed to a digital pre distortion (DPD) circuit, and fed to a carrier leakage suppression block 101'.

The thus-compensated digital signal may then be transmitted using a standard direct conversion wideband radio transmitter architecture 100'; its I and Q components may be fed to a digital-to-analog converter (DAC) and converted, the analog I and Q signal outputs of the DAC may then be low-pass filtered, mixed in CIF-RF mixer with a carrier frequency signal $F_c(t)$, amplified and transmitted via the antenna.

A conceptual example of the I/Q imbalance correction is shown in boxes 107',108'; in box 107' the power spectral density of the signal transmitted from the radio 100' shows the composite FHSS-MA signal composed of multiple FHSS signals transmitted simultaneously. The direct conversion radio I/Q path's imbalance is generating non-desirable image transmissions which may not meet communications standards and/or regulations. Once the imbalance at each of these FHSS channels is corrected by its respective I/Q imbalance correction block 102', the undesirable image signal is attenuated as shown in box 108'.

In FIG. 3B two or more frequency hopping waveforms frequencies $F_i(t)$, $F_j(t)$ may be identical due to the random nature of their selection (e.g. in Bluetooth® frequency hopping selection is pseudo-random). In such a scenario enabling the transmission of data in paths I and j may not be desirable to avoid false co-channel reception, and power control block 109' may disable transmission on both paths or on a particular path (for example by controlling the amplitude Ai and/or Aj of the corresponding transmit paths) according to priority set by the device manager 15 shown in FIG. 2D (which may be based on comparative measure (e.g. power level, bit error rate, synchronous/non-synchronous data) between the paths).

In yet a further example, as shown in FIG. 3A-3B, FHSS-hotspot 1 may take advantage of common frequencies to rearrange the functionalities of the FHSS-hotspot and a collocated WLAN device. It is noted that WLANs may be supported in the same frequency band as FHSS-MA (e.g. WLAN and Bluetooth® sharing the 2.4 GHz band); therefore, as shown in FIG. 3A-3B, the WLAN and FHSS-hotspot may use common wideband digital front end 10,10', analog & 2.4 GHz RF circuitry. The possibility of using common wideband analog & 2.4 GHz RF circuitry is facilitated by the fact that the full 2.4 GHz band (i.e., ~80 MHz bandwidth) may be supported by the analog circuitry, so it may thus be possible to simply include additional digital processing capabilities to accommodate the WLAN in that band.

It is further noted that one or more of the operations of the digital front end as shown in FIGS. 3A and 3B, may be implemented by means of one or more processors and associated software instructions that may cause the one or more processors to implement the operations (e.g. coefficients calculation 104,104').

Figure 4A:
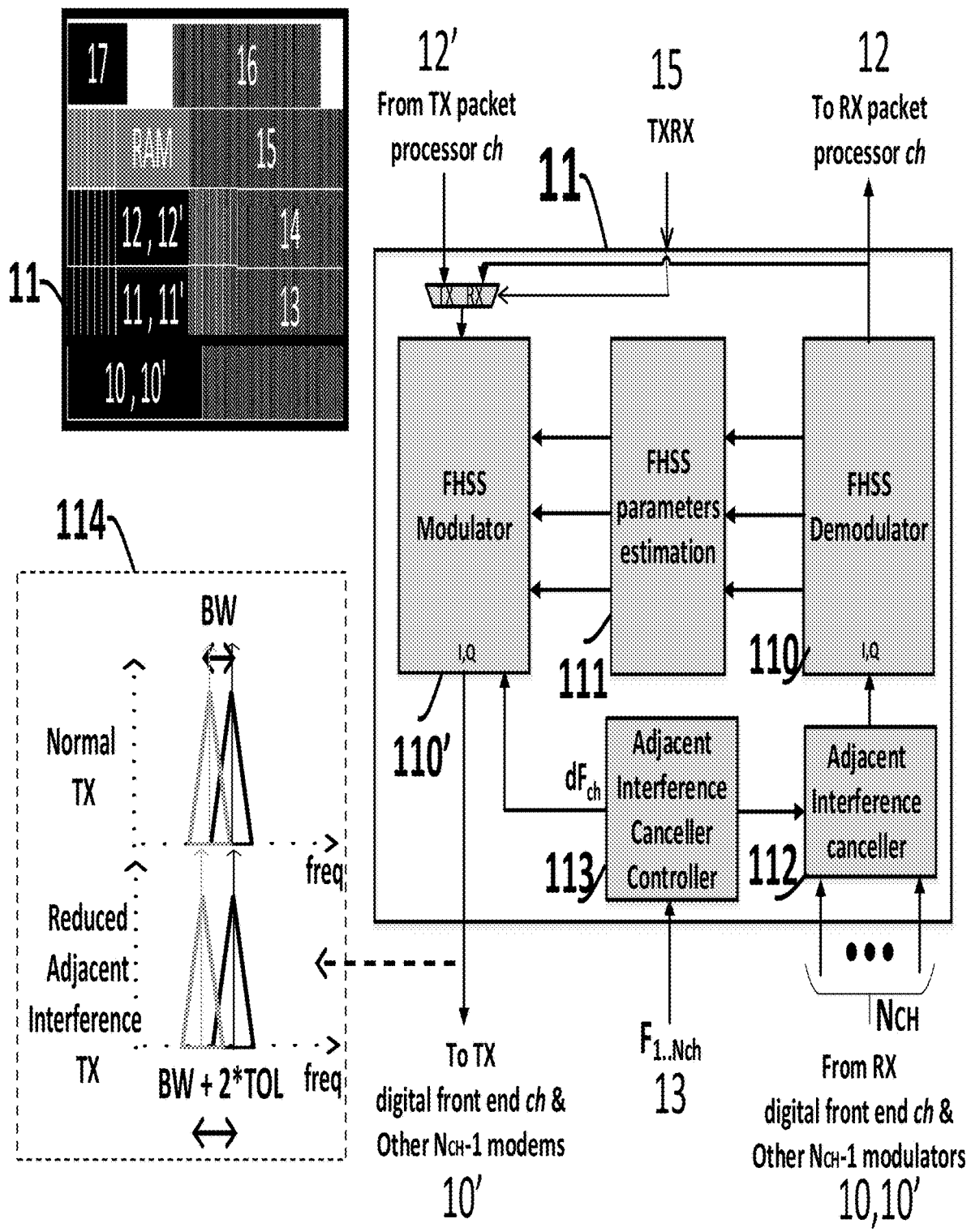
FIG. 4A-4B show a conceptual block diagram of a FHSS-hotspot adjacent-channel-rejecting modem according to an aspect of the disclosure.
Figure 4B:
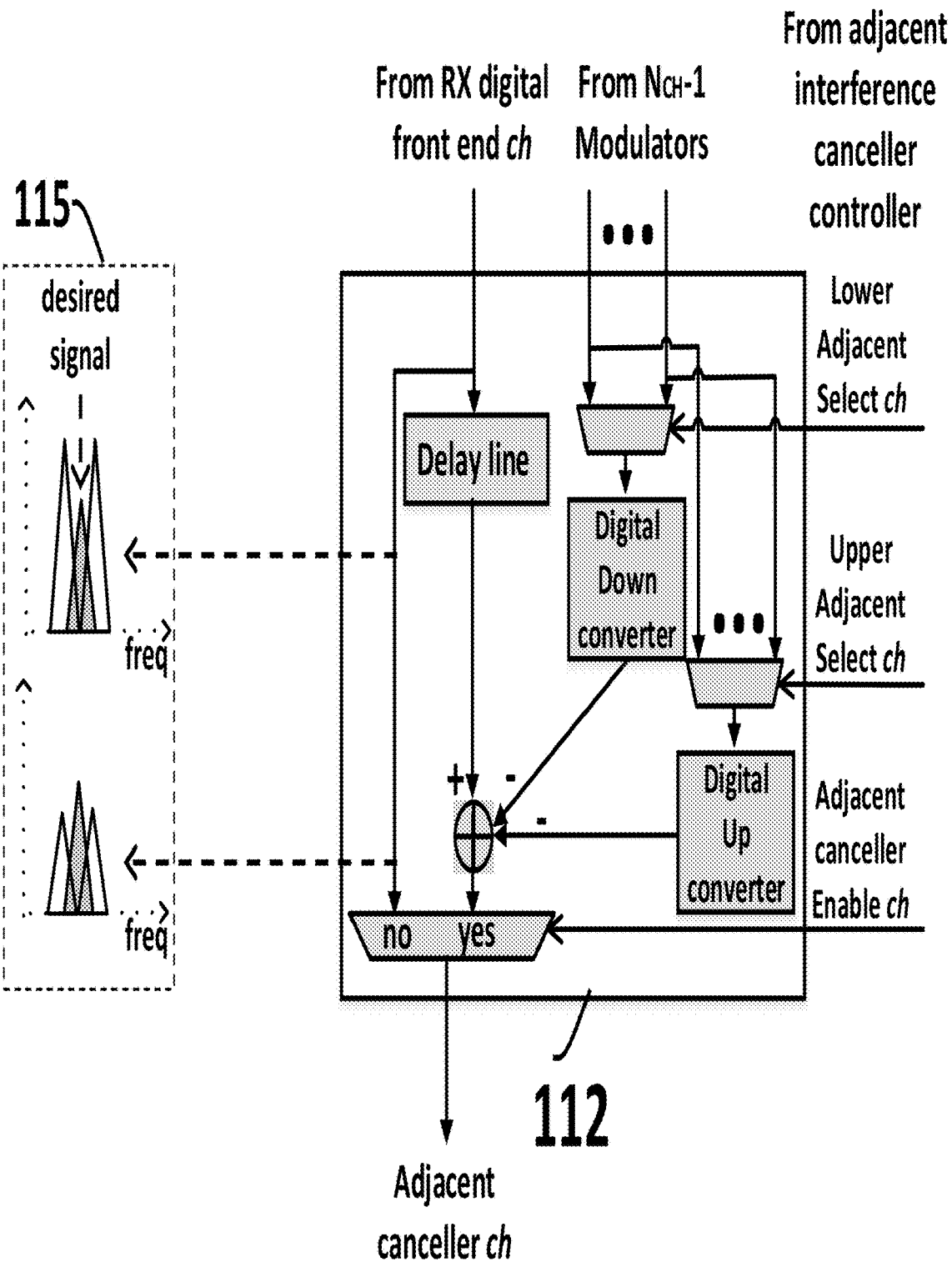

FIGS. 4A, 4B show a conceptual block diagram of a FHSS-hotspot adjacent-channel-rejecting modem. Due to the low immunity of a conventional FHSS modem (modulator and demodulator) to adjacent channel interference in dense channel deployments (e.g. in Classic Bluetooth® channel bandwidth approximately equals the signal bandwidth), the number of FHSS devices that may communicate concurrently in a given band may be too low to support certain multi-device applications. To increase the number of devices that may communicate concurrently it may be desirable to develop a modem that is able to reject FHSS adjacent channel interference. Such modem is referred to as adjacent-channel-rejecting (ACR) modem.

FIG. 4A shows a conceptual diagram of a respective ACR modem apparatus 11 fed by the respective digital receive path ch of digital front end apparatus 10 in FIG. 2D. The interference canceller apparatus 112 in FIG. 4B may be initially disabled by interference canceller controller apparatus 113 such that it is effectively bypassed and the incoming signal is directly output to the FHSS demodulator apparatus 110. Once the respective FHSS signal is detected and demodulator apparatus 110 starts demodulating it, the FHSS signal parameters estimator apparatus 111 updates the FHSS signal's parameters relevant for the FHSS signal's re-modulation, which may include yet are not limited to the signal's amplitude, delay, phase, symbol rate, modulation index (e.g. in Bluetooth® Classic may vary between 0.28-0.35), matched filter mismatch and received data. The signal is then regenerated using a respective FHSS modulator apparatus 110' (which may be the same modulator used during transmission as shown in FIG. 4A) using the estimated parameters.

Once a signal adjacent to the respective received signal is detected, demodulated and regenerated; if it is stronger than the respective received signal, interference canceller apparatus 112 may be enabled by interference canceller controller apparatus 113 such that the adjacent channel's interference is mitigated (as shown in FIG. 4B box 115). Two or more interference canceller apparatuses 112 may be concatenated to form an improved serial interference canceller.

During multi-channel FHSS transmission, the respective FHSS modulators 110' of two adjacent channels (or their respective up converters in the transmit digital front end apparatus 10') may reduce the cross interference between themselves by increasing their carrier frequency separation by up to two times the carrier frequency tolerance allowed by a receiver (depending on the FHSS-hotspot device frequency accuracy), as shown in FIG. 4A box. 114. Interference canceller controller apparatus 113 may set the respective carrier frequency offset $dF_{ch}$.

It is further noted that one or more of the operations of the FHSS adjacent-channel-rejecting (ACR) modem apparatus 11, as shown in FIGS. 4A and 4B, may be implemented by means of one or more processors and associated software instructions that may cause the one or more processors to implement the operations (e.g. FHSS signal parameters estimation).

Figure 5:
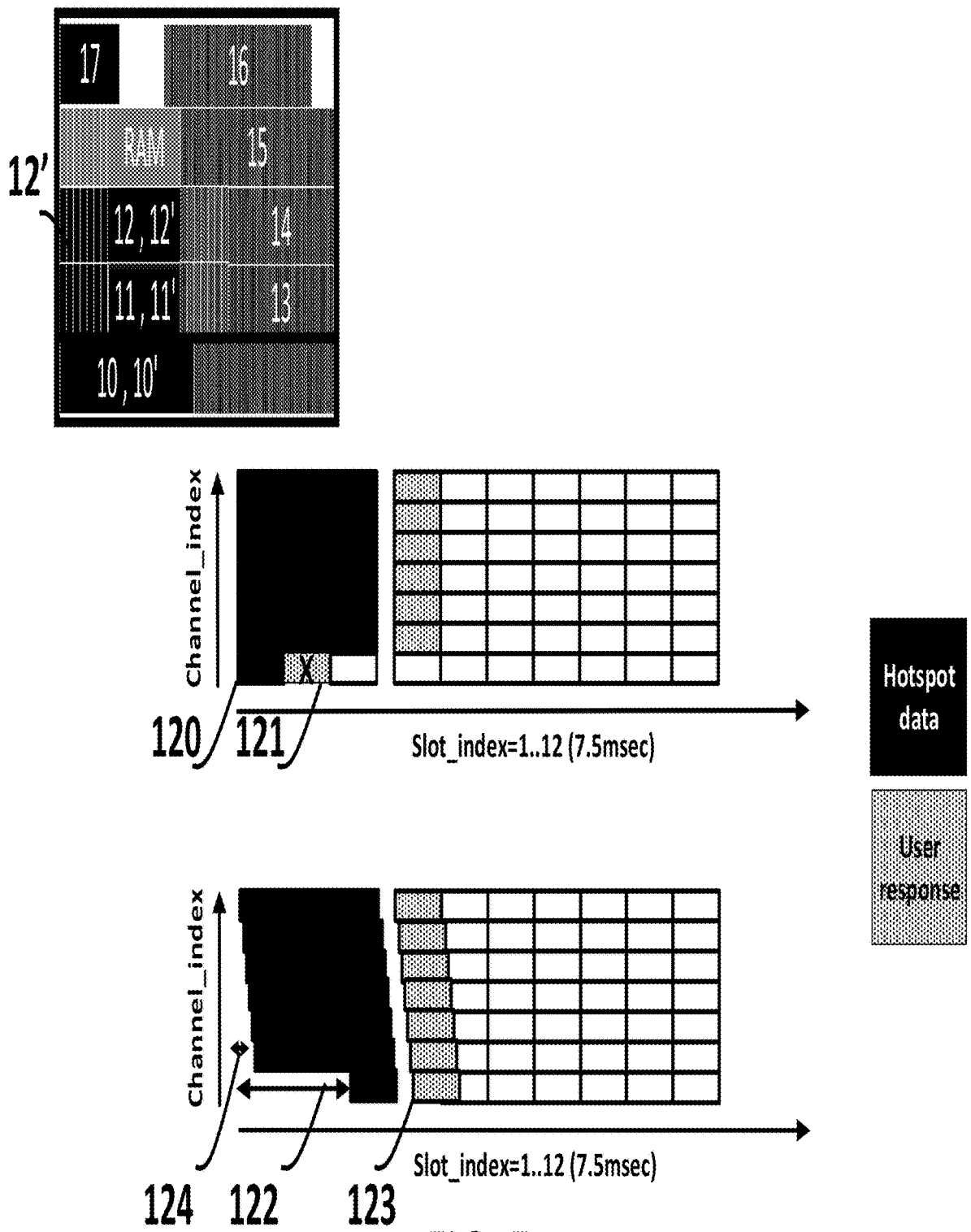
FIG. 5 shows a conceptual example of FHSS-hotspot transmission delay technique according to an aspect of the disclosure.

FIG. 5 shows two conceptual examples of Nch (e.g. 7) FHSS transmit paths transmitting packets simultaneously. In both cases a respective FHSS transmit path's packet 120 output by packet processor 12' in FIG. 2D has shorter duration than other FHSS transmit paths packets. In the first example all packets are scheduled to be transmitted at the same TX instant (that may be set by device manager 15); as result, the respective receive path may not be able to receive the respective FHSS device acknowledgement 121 in case of FHSS-hotspot half-duplex operation (i.e. time-division-duplex (TDD)).

In the second case, the respective FHSS transmit path packet processor 12' may delay 121 its packet transmission (e.g. in the case of Bluetooth® classic delay 121 may be 1.25 msec (2 Bluetooth® classic slots as shown) or 2.5 msec (4 Bluetooth® classic slots)) to allow the respective FHSS device to acknowledge its reception after the TDD FHSS-hotspot device already switched to reception, thus allowing itself to receive the acknowledgment packet 122 reliably and avoid retransmission.

By being able to communicate concurrently using both shorter and longer packets (e.g. 1-slot and 3-slot packets in Bluetooth® Classic) with proper packet delay settings, link control and management packets which are usually short may be transmitted concurrently with longer data packets. This implies that in cases where some FHSS-hotspot channels are occupied with control and management of their devices, other FHSS channels may not need to lower their data transfer rate.

By being able to communicate concurrently using both shorter and longer packets (e.g. 1-slot and 3-slot packets in Bluetooth® Classic) with proper packet delay settings, more than a single session type may be supported (hybrid session). For example, a Classic Bluetooth® device supporting human interface device profile (HID) (e.g. mouse/keyboard/controller) may communicate simultaneously with a Classic Bluetooth® device supporting the advanced audio distribution profile (A2DP).

A respective transmit path's packet processor 12' may delay 124 its output relative to other transmit paths packet processors outputs also to avoid simultaneous transmission of the transmit paths (thus to avoid violating standard/regulatory spectral mask requirements), and/or to enable improved operation of the ACR modem shown in FIGS. 4A, 4B by enabling the concatenation of interference canceller apparatuses 112 (possible due to the respective delays between the received signals).

Figure 6A:
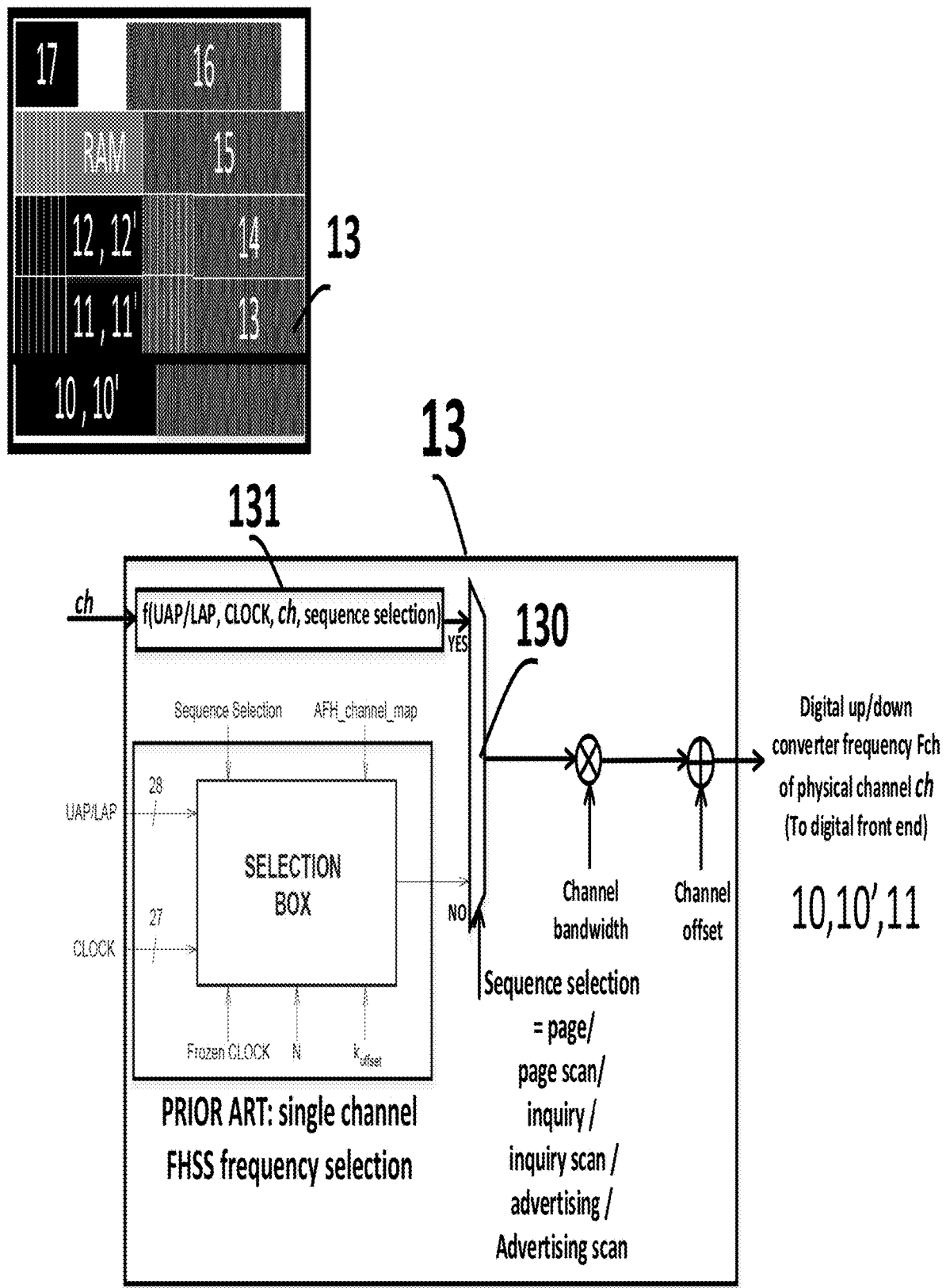
FIG. 6A-6B show conceptual examples of FHSS-hotspot multi-channel-signaling frequency selection and scheduling techniques according to an aspect of the disclosure.
Figure 6B:
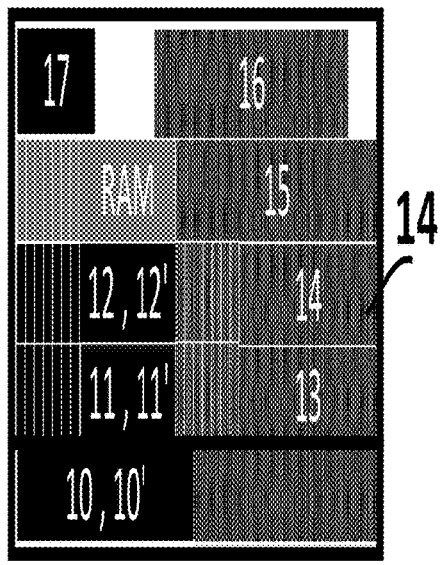
Figure 6B:
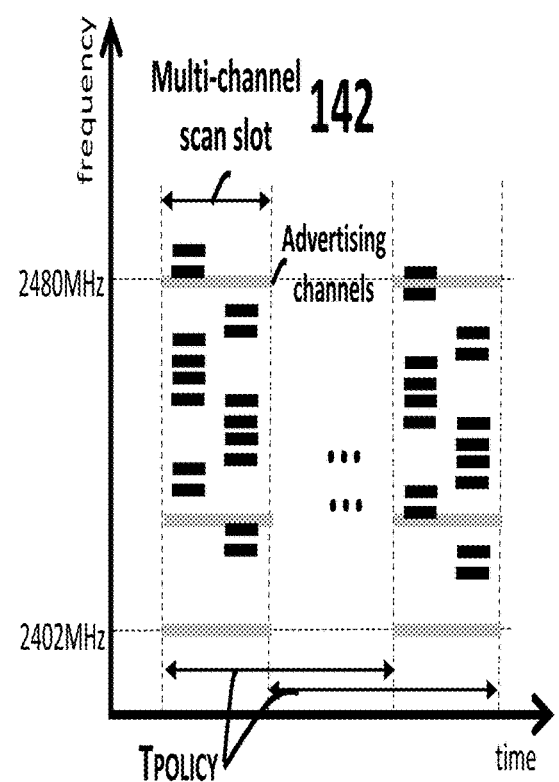
Figure 6B:
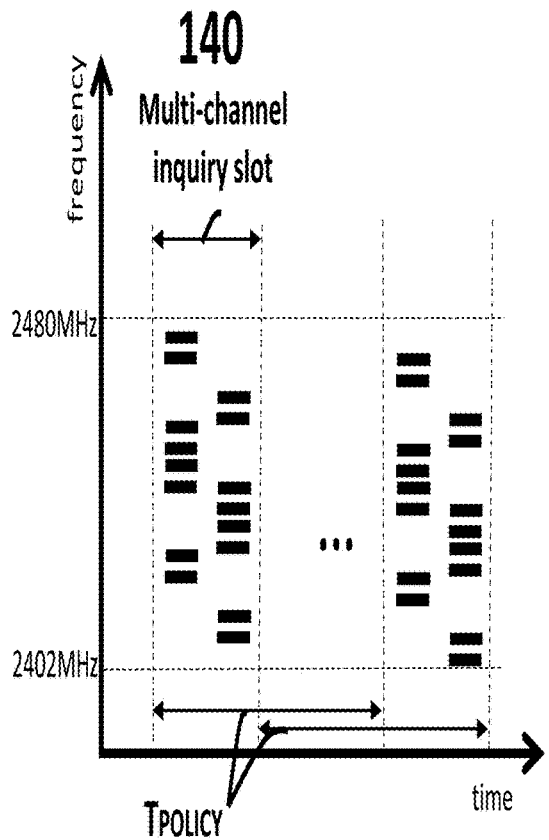
Figure 6B:
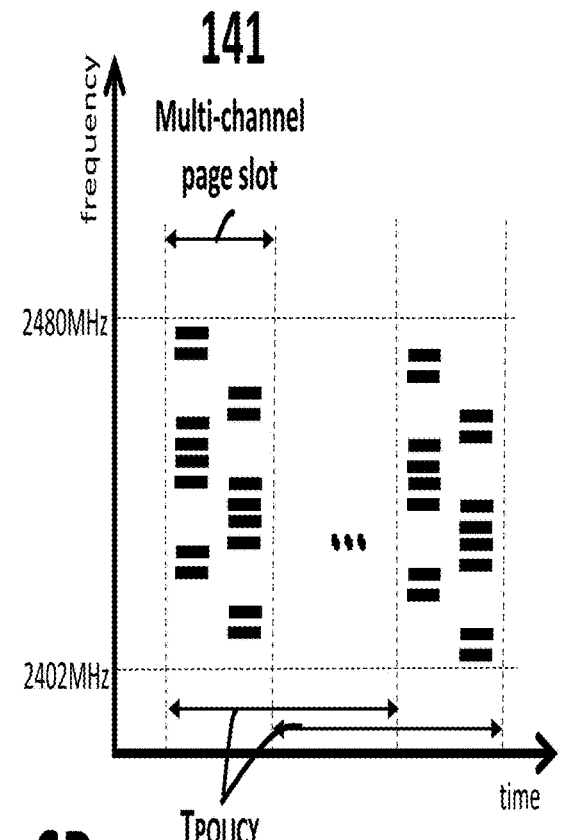

FIGS. 6A, 6B show conceptual examples of FHSS-hotspot multi-channel-signaling and multi-channel-scanning frequency selection and scheduling technique. FIG. 6A shows a conceptual example of a respective FHSS channel ch frequency selection box 13 in FIG. 2D. In order to speedup connection to a FHSS device during an ongoing multi-device session, FHSS-hotspot device may assign its FHSS channels to different frequencies (channels) during signaling and/or during scanning using multiplexer 130 and a function in which the digital path index ch is a parameter 131.

In the specific case of Classic Bluetooth®, by using Nch=16 FHSS channels, the FHSS-hotspot device link controller 14 in FIG. 2D may signal on all the 32 frequencies allocated for signaling within a single Bluetooth® time slot (625 usec) as shown in FIG. 6B boxes 140,141 and scan all the 32 frequencies allocated for signaling response within a single Bluetooth® time slot (625 usec) as shown in FIG. 6B boxes 142. By repeating the signal and scan every time interval $T_{POLICY}$ that is smaller or equal than the minimal FHSS device scan duration (~10 msec), it is highly probable that the scanning FHSS device and FHSS-hotspot manage to exchange signaling and connect within a fraction of a second during an ongoing multi-device session.

In the specific case of Bluetooth® Low Energy, the FHSS-hotspot device 1 may allocate 3 FHSS channels to scan for advertising packets of multiple FHSS devices as shown in FIG. 6B box 142. In parallel to scanning for advertising packets, the FHSS-hotspot device 1 may communicate with other devices. Such multi-channel periodic scanning may speedup connection and/or reduce FHSS devices power consumption (e.g. by possibly tripling their advertising interval).

Figure 7:
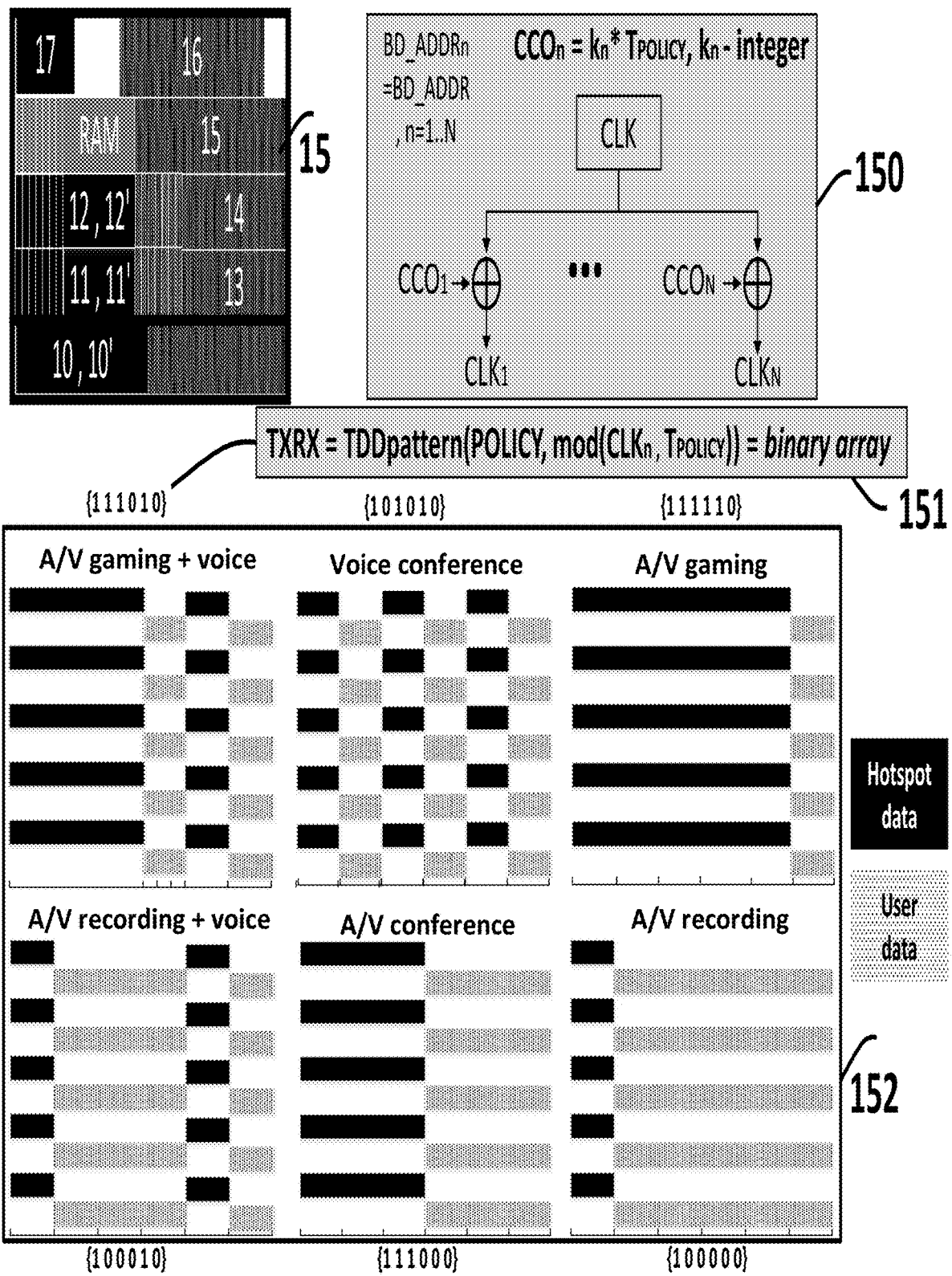
FIG. 7 shows conceptual examples of FHSS-hotspot device TX/RX patterns and FHSS clocks generation according to an aspect of the disclosure.

FIG. 7 shows conceptual examples of a FHSS-hotspot TDD device manager 15 TX/RX patterns and FHSS clocks generation. The FHSS-hotspot device 1 may be able to avoid simultaneous transmission and reception of respective transmit and receive paths, by a-priori subdividing a periodic time interval allocated for data transmission (e.g. 3.75 msec in Classic Bluetooth®) to fixed time slots (e.g. 625 usec in Classic Bluetooth®) assigned for either transmission or reception of data according to a binary TX/RX pattern a-priori set as a function 151 of the FHSS-hotspot's application, and scheduling all of its data packets transmissions and receptions according to that TX/RX pattern.

Six different examples of FHSS-hotspot TX/RX patterns for supporting corresponding Classic Bluetooth® multi-device applications are shown in box 152 in FIG. 7. The TX/RX binary pattern length is set to 6, corresponding to 6 time slots allocated in the periodic 3.75 msec data transmission time interval. In the voice conference applications, for example, the TX/RX pattern assigned is {1 0 1 0 1 0} due to the symmetrical TX and RX data rates (64 Kbps) and due to the high reliability required (up to 2 packet repetitions in 3.75 msec).

The FHSS-hotspot device may use a single device address (e.g. Bluetooth® BD_ADDR) to be able to connect to FHSS devices that already established a bond with the FHSS-hotspot device (by storing each other's relevant parameters in a non-volatile memory) during its operation as a single FHSS channel device (e.g. Bluetooth® master device). As a result, in case the hop frequency is a function of both the FHSS device address and a FHSS clock (such as in Classic Bluetooth®) it may not be possible to use a common FHSS clock for all FHSS connections to minimize channels frequencies overlap. In order to still be able to align the FHSS connections TX/RX patterns, the relationship between the FHSS clocks may be as shown in box 150; the FHSS clocks are cyclically offset relative to each other by integer multiple of the time interval Tpolicy (for example in Bluetooth® Classic Tpolicy is usually 7.5 msec) which is greater or equal to the time interval allocated for data transmission (e.g. 3.75 msec).

The FHSS-hotspot device may be able to rapidly connect to additional FHSS devices during a session, by dividing time to fixed time intervals Tpolicy ("FHSS-hotspot Policy's time interval") which may further be subdivided to a first sub-interval that is assigned to periodic transmission or reception of data according to the TX/RX pattern, and a second sub-interval that is assigned to none-periodic/one-time transmission or reception required to control communications e.g. establish connection (and/or assigned to a co-located device (e.g. WLAN) communications to allow concurrent communications of both devices).

Figure 8A:
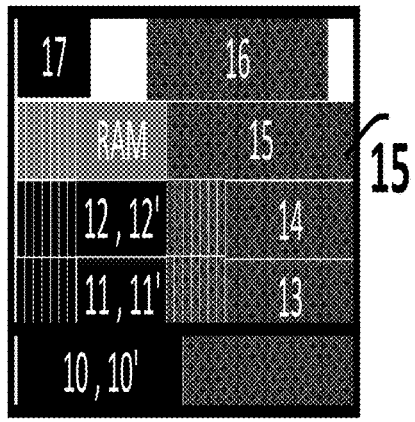
FIGS. 8A-8B show conceptual examples of FHSS-hotspot concurrent communications with multiple commercially available FHSS devices.
Figure 8A:
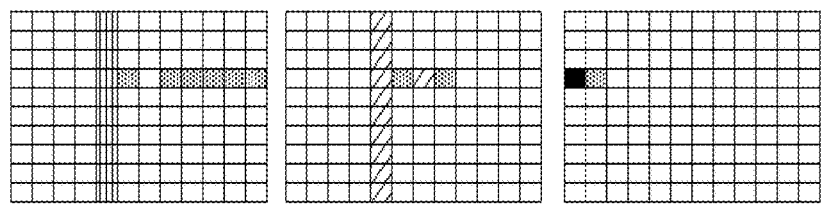
Figure 8A:
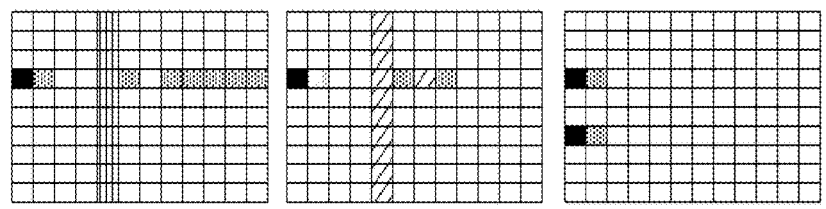
Figure 8A:
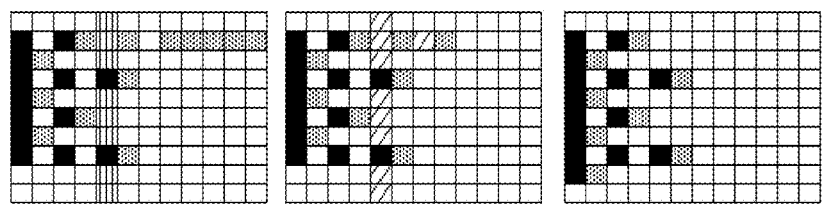
Figure 8A:
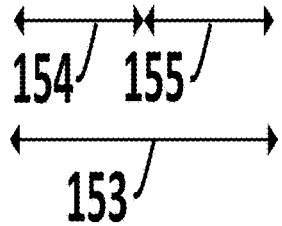
Figure 8B:
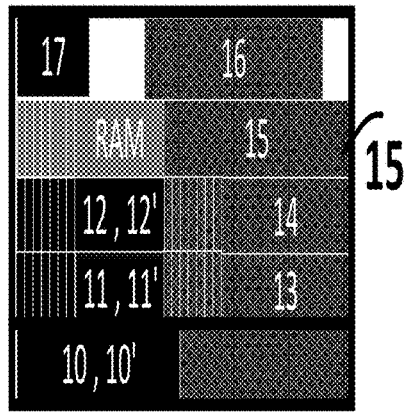
Figure 8B:
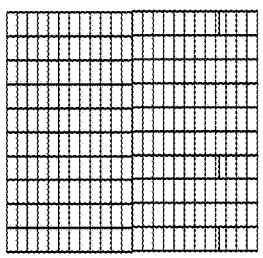
Figure 8B:
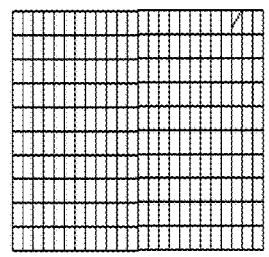
Figure 8B:
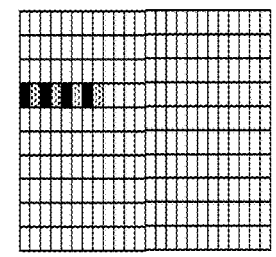
Figure 8B:
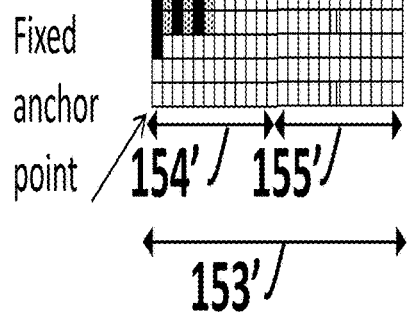
Figure 8B:
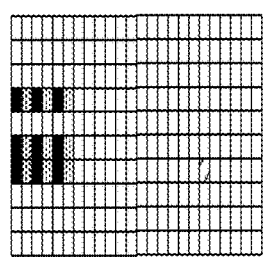
Figure 8B:
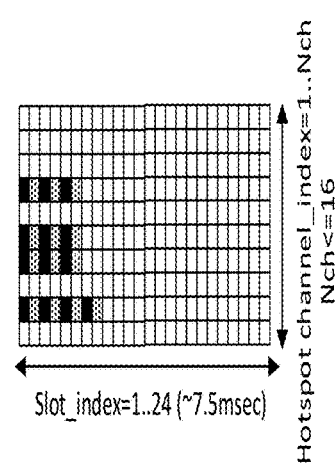

FIGS. 8A, 8B show two conceptual examples of FHSS-hotspot device concurrent communications with multiple Bluetooth® devices; FIG. 8A shows FHSS-hotspot device concurrent communications with multiple Bluetooth® Classic devices, and FIG. 8B shows FHSS-hotspot device concurrent communications with multiple Bluetooth® Low Energy devices.

In FIG. 8A Tpolicy 153 equals 7.5 msec, data transmission interval 154 equals 3.75 msec, Nch equals 16. The time period assigned for none-periodic/one-time transmission 155 is Tpolicy-data transmission interval=3.75 msec and is used to control communications. FHSS-hotspot device initiates communications by inquiring and paging as shown in FIG. 6B boxes 140,141. It then establishes connections sequentially such that all Bluetooth® Classic connections may be established within few seconds.

In FIG. 8B Tpolicy 153' equals 7.5 msec, data transmission interval 154' equals ~3.75 msec, Nch>=3. The time period assigned for none-periodic/one-time transmission 155' is Tpolicy-data transmission interval=~3.75 msec and is used to control communications. FHSS-hotspot device initiates communications by multi-channel scanning for advertising packets as shown in FIG. 6B box 142. It then establishes connections sequentially such that all Bluetooth® Low Energy connections may be established within a fraction of a second. This example assumes the packet payload lengths of all Bluetooth® Low Energy devices connected to the FHSS-hotspot device 1 are identical (e.g. 20 bytes).

Figure 9:
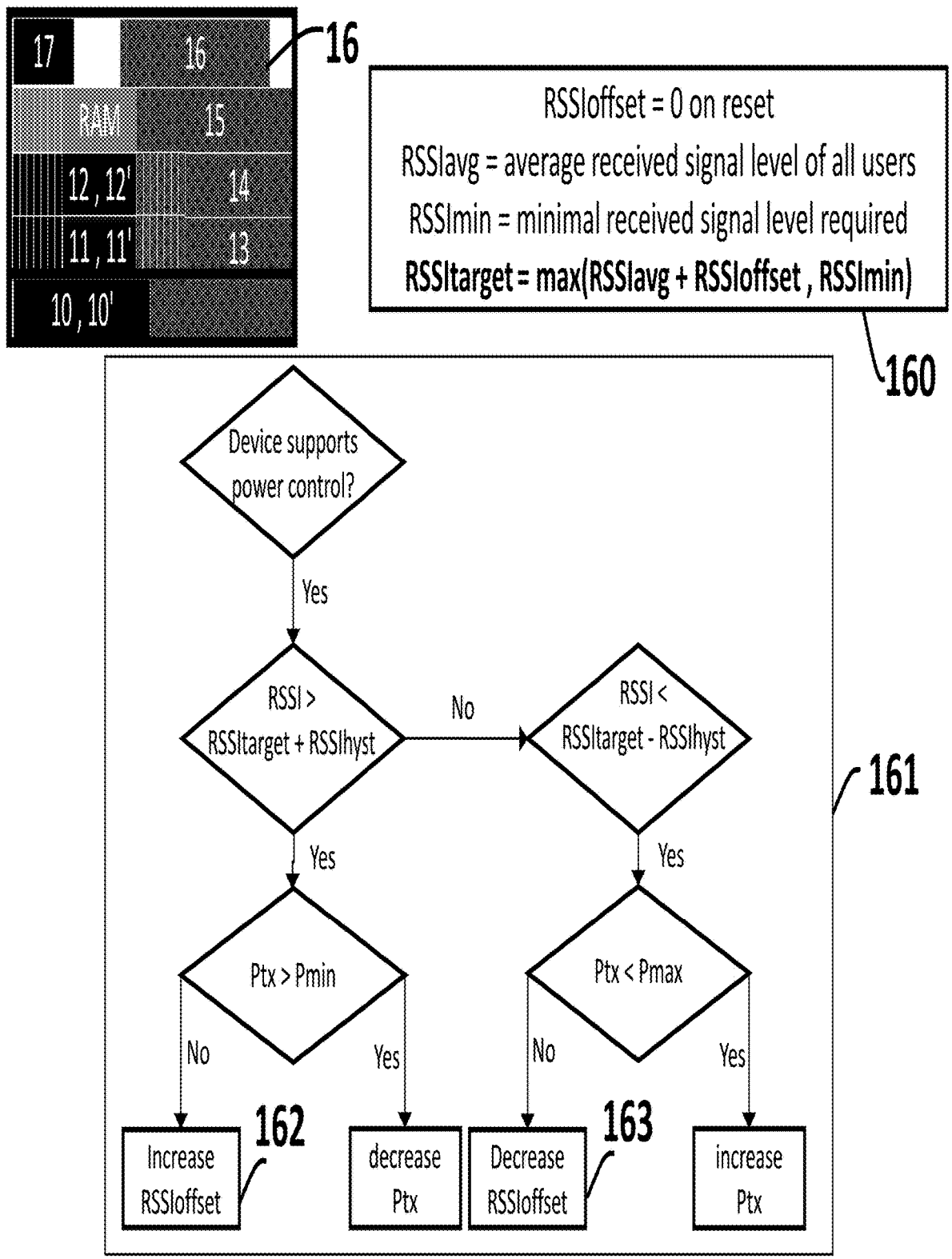
FIG. 9 shows a conceptual flow chart of a FHSS-hotspot power control technique of multiple FHSS devices according to an aspect of the disclosure.

FIG. 9 shows a conceptual flow chart 161 of a FHSS-hotspot power control technique of a respective FHSS device (e.g. Bluetooth® device). The FHSS-hotspot device link manager 16 may mitigate cross interference between adjacent signals to increase the number of devices that may operate reliably over a given frequency band, by applying a multi-device power control technique that equalizes the average received power and average transmitted power of its FHSS connections. Link manager 16 may only control the transmit power of FHSS devices that support transmit power control feature. The target signal level on the receive side may be set as shown in box 160; in cases where a respective FHSS device transmit power is out of bounds 162,163, the target signal level is offset to try to keep the device's transmit power in bound and by that improving equalization of averaged received power.

Figure 10:
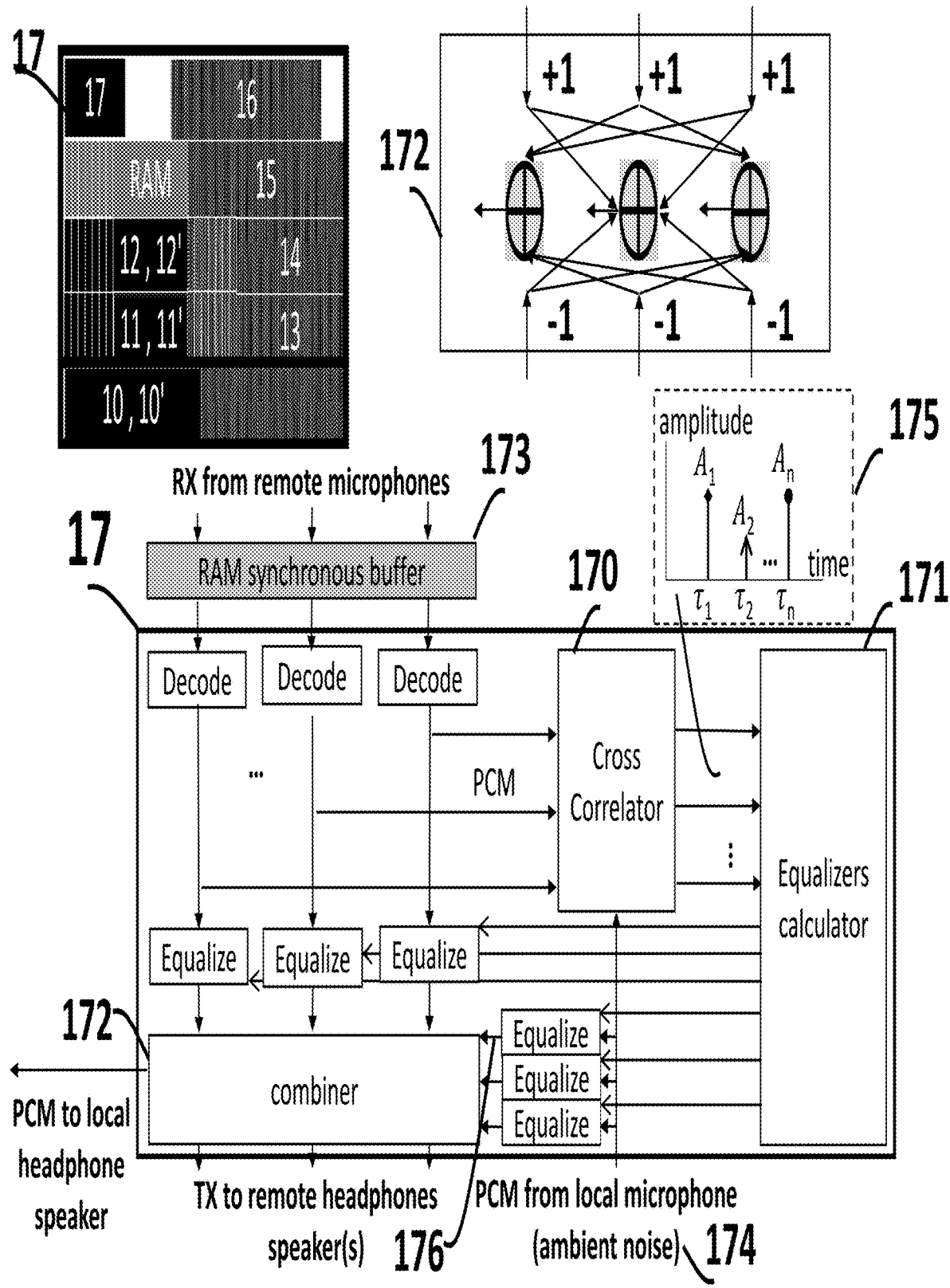
FIG. 10 shows conceptual block diagram of FHSS-hotspot audible ambient noise cancellation according to an aspect of the disclosure.

FIG. 10 shows conceptual block diagram of FHSS-hotspot device ambient noise cancellation which may be performed by the low-latency media processor 17. In cases where the FHSS device has limited noise cancelling capabilities (e.g. Bluetooth® miniature microphone, speaker, headset) the FHSS-hotspot device may further be able to mitigate audible ambient noise in its surrounding by proper blending (filtering and adding) of multiple FHSS devices' microphone signals that are concurrently received over corresponding multiple wireless synchronous connections (e.g. over Bluetooth® (e)SCO channel) and the FHSS-hotspot device's local microphone.

Each Tpolicy time interval (153 FIG. 8A) multiple microphones data frames may be concurrently retrieved from the RX synchronous buffer(s) 173 and from the local microphone buffer 174. A respective FHSS device microphone data frame which is dominated by ambient noise (e.g. the FHSS-hotspot local microphone signal 174) may be converted to audio samples, properly filtered (equalized) and subtracted from a an active microphone signal using combiner block 172. Example of a combiner block 172 that mitigates the ambient noise during a localized recording/teleconference/gaming session using three (non noise-cancelling) headsets is shown in FIG. 10.

The filters (equalizers) may be calculated by equalizers calculator block 171 using various methods. For example, the cross correlation between the signals may be used as a metric for calculating the equalizers and picking the respective microphone signal (which is dominated by ambient noise) to be subtracted from the linear combination of active microphone signals. In box 175 the cross correlation between ambient noise dominated microphone signal (e.g. the FHSS-hotspot local microphone signal 174) and the three headsets microphone signals is shown assuming a single-tone ambient noise with negligible echo; by setting the noise equalizers such that similar ambient noise delay and amplitude incurring in their corresponding headset microphones, the respective equalized noise signal 176 may be subtracted from corresponding headset microphones as shown in 172 and single-tone ambient noise may be mitigated.

Figure 11:
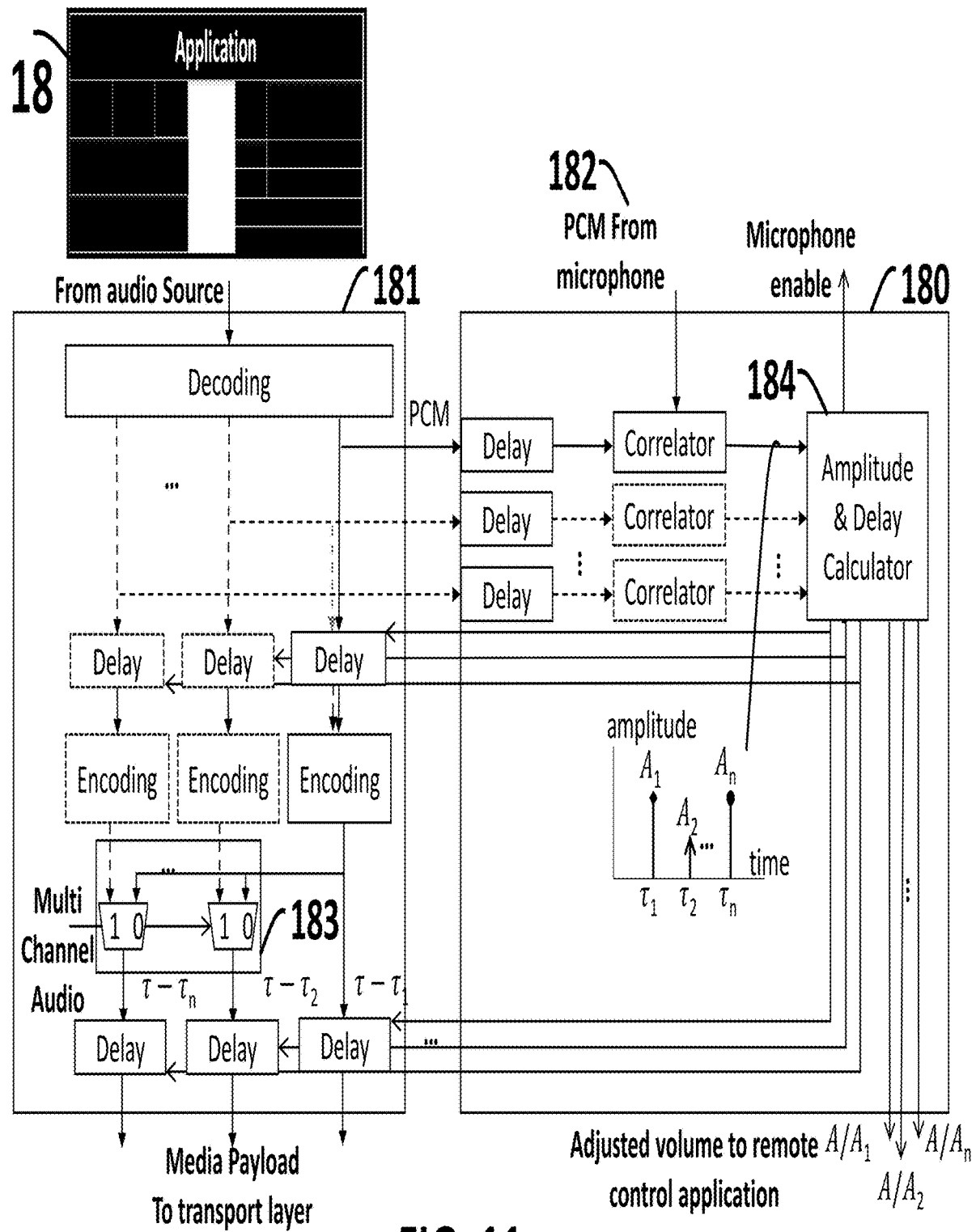
FIG. 11 shows a conceptual block diagram of FHSS-hotspot adaptive acoustic beam forming according to an aspect of the disclosure.

FIG. 11 shows a conceptual block diagram of FHSS-hotspot device short range adaptive acoustic beam forming which may be performed by application processor 18. The FHSS-hotspot device may continuously balance the delay and volume (online calibration) of the audio streams transmitted to plurality of FHSS speakers that may be moving relative to it, based on the FHSS-hotspot device's microphone 182 input and/or the speakers' microphones inputs. The audio streams data 181 and control 180 planes are shown in FIG. 11.

In the case of a single audio stream (e.g. multi-channel-audio is 0 in 183), the FHSS-hotspot device may continuously move the virtual audio source location relative to itself/the other FHSS devices to create 3D sound effects, by continuously adapting the delay and volume of the audio streams of speakers that may be moving relative to it, based on the FHSS-hotspot device's microphone 182 input and/or the speakers' microphones inputs.

The delays and amplitudes may be calculated by amplitude and delay calculator block 184 using various methods. For example, the correlations between a microphone signal (e.g. the FHSS-hotspot local microphone signal 182) and the audio streams signals may be used as a metric for updating the delays and amplitudes of the streams. In box 175 the correlation between three audio streams signals and a microphone signal is shown; beamforming may be achieved by trying to equalize the correlations delays and amplitudes (by adjusting the delays and amplitudes of the audio streams).

Figure 12:
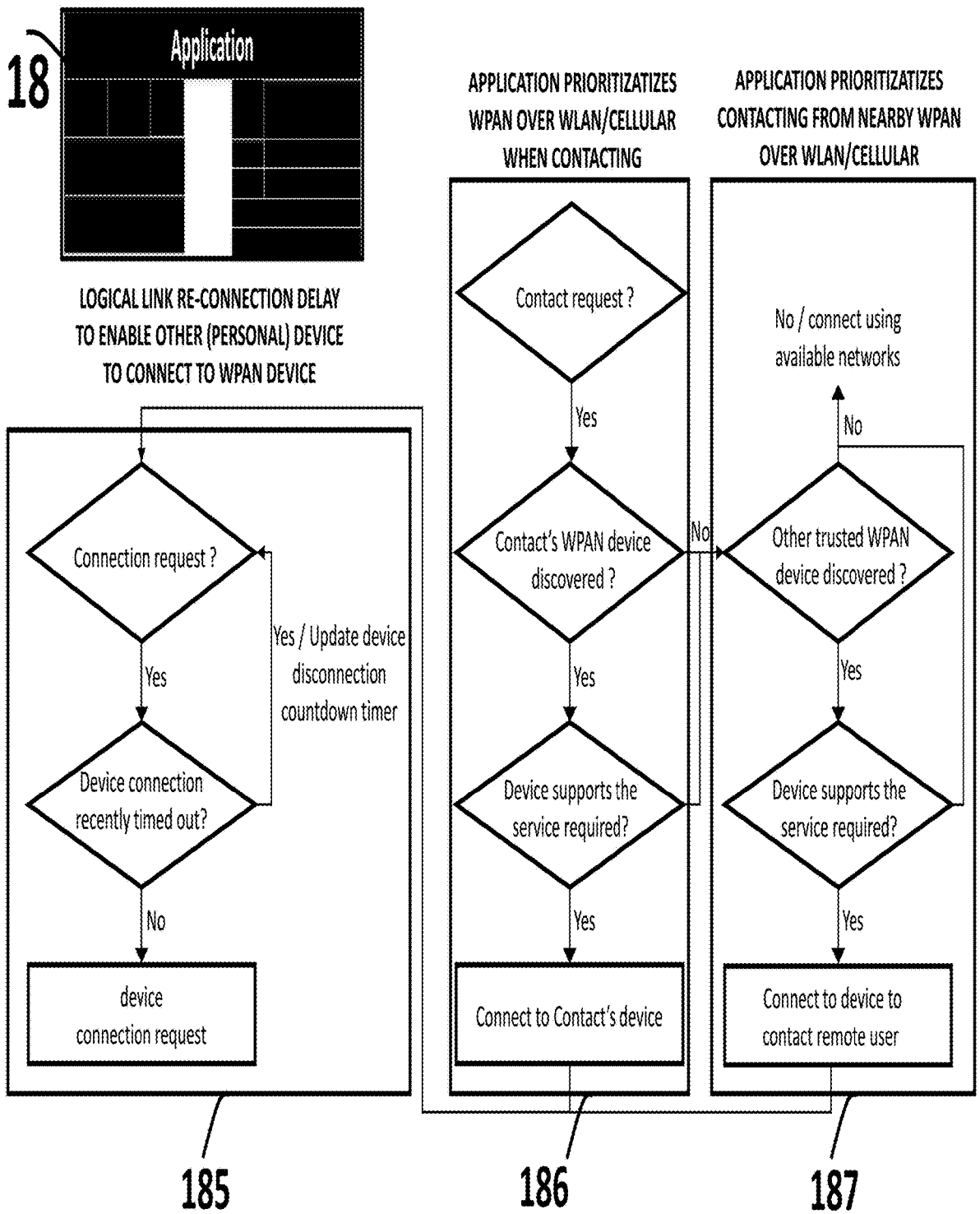
FIG. 12 shows a conceptual flow chart of a method of connecting to a device and conceptual flow charts of contacting a person according to aspects of the disclosure.

FIG. 12 shows a conceptual flow chart 185 of a method to connect a FHSS device (e.g. the FHSS-hotspot device) to another FHSS device, and conceptual flow charts 186,187 of methods in which a FHSS device (e.g the FHSS-hotspot device) may contact a person. The FHSS-hotspot device may delay reconnection to a FHSS device that lost connection (rather than disconnected) as shown in flow chart 185, to enable other (personal) device to connect to the FHSS device. Reconnection delay may be required for example when the user of the FHSS device wishes to re-pair and re-connect to his personal device.

A FHSS device (including the FHSS-hotspot device) may associate a short range FHSS communications device address (e.g. Bluetooth® device number) with a person, and try to contact the person by first trying to connect to the person's associated short range FHSS device (provided it supports the service required) as shown in conceptual flow chart 186.

A FHSS device (including the FHSS-hotspot device) may contact a person by first trying to connect to a trusted personal FHSS device in its proximity that supports the service required to contact that person (thus acting as a wireless bridge), to reduce electromagnetic-microwave-radiation compared to other wireless communications techniques (e.g. WLAN, cellular), as shown in conceptual flow chart 187.

Figure 13:
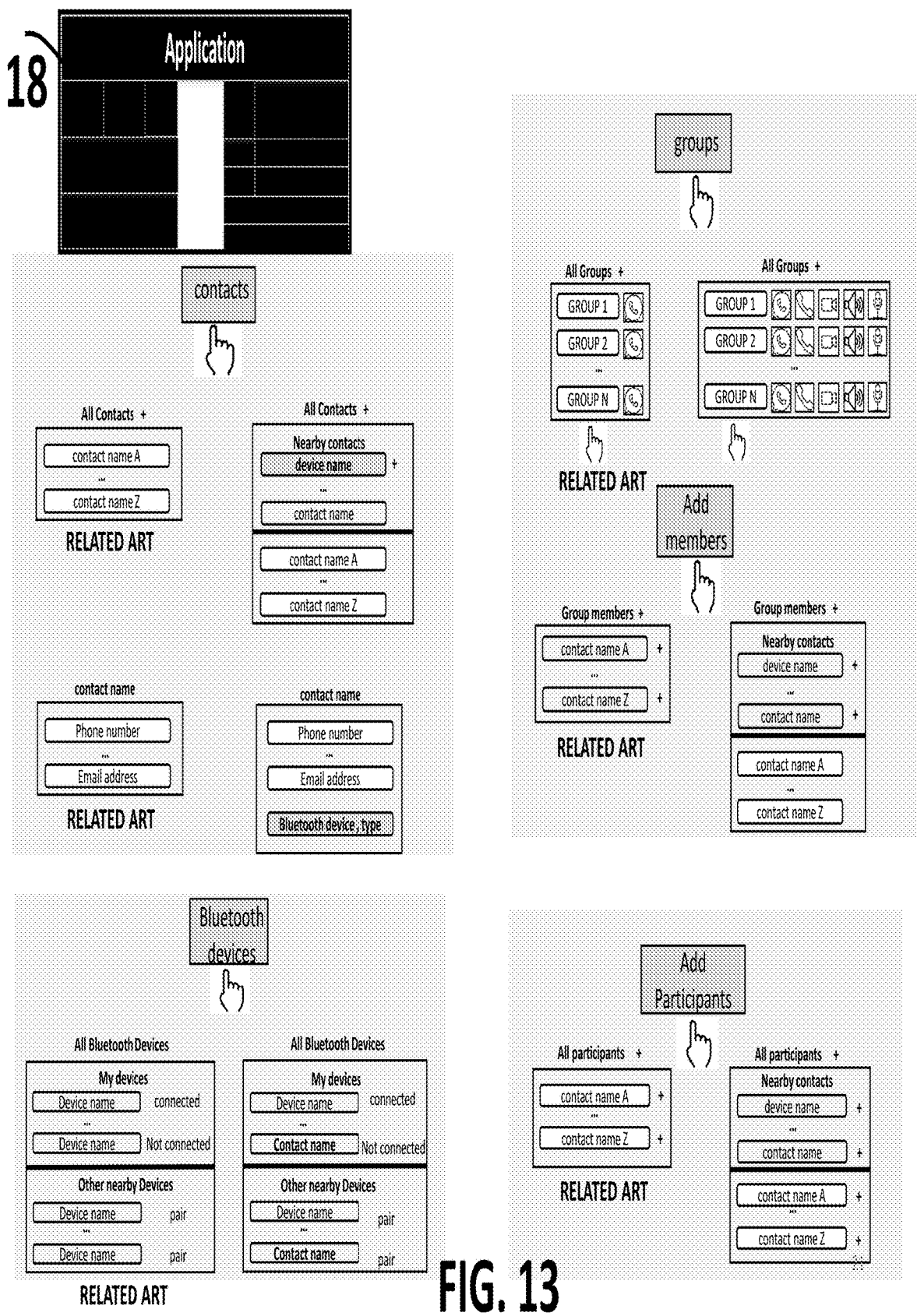
FIG. 13 shows a conceptual user interface for associating short range devices with contacts, according to an aspect of the disclosure.

FIG. 13 shows conceptual user interfaces assuming short range FHSS devices are associated with contacts. The FHSS devices discovered may appear in the contact list and may be associated with specific contact by adding the relevant device details to the contact details (e.g. the contacts details may include phone number, address and Bluetooth® device name/address/class).

It will be appreciated by persons skilled in the art that the present invention is not limited by what has been particularly shown and described hereinabove. Rather the scope of the present invention includes both combinations and sub-combinations of various features described hereinabove as well as modifications and variations which would occur to persons skilled in the art upon reading the foregoing description and which are not in the prior art.

What is claimed is:

1. A frequency-hopped spread-spectrum (FHSS) signals wireless receiver apparatus, comprising:
   An antenna that receives a signal comprising multiple FHSS signals, and
   A radio frequency (RF) synthesizer that generates a synthesized radio frequency, and
   A RF downconverter that down-converts the signal using the synthesized radio frequency to an intermediate frequency (IF) signal, and
   at least one wide band select filter with bandwidth greater-than at least 5 times the bandwidth of each of the FHSS signals, that filters the IF signal to reject out-of-band interference and outputs a filtered signal, and
   At least one analog to digital converter that converts the filtered signal to a digitized signal, and
   A I/Q imbalance correction circuit that inputs the digitized signal and outputs an array of multiple FHSS intermediate frequency (IF) I and Q signals using an array of coefficients, and
   an array of IF downconverters that down-converts the array of FHSS IF I and Q signals to an array of FHSS zero-IF (ZIF) or low-IF (LIF) signals, and
   an array of channel filters that filters the array of FHSS ZIF or LIF signals and outputs an array of FHSS baseband signals, and
   An array of demodulators that demodulate their respective baseband signals to demodulated data.

2. The apparatus of claim 1, wherein FHSS intermediate frequency (IF) I and Q signals imbalance is corrected using coefficients that are determined as a function of their respective FHSS signal's carrier frequency.

3. The apparatus of claim 1, further comprising a coefficients memory configured to output coefficients to be used to correct the imbalance between the FHSS intermediate frequency (IF) I and Q signals, wherein the coefficients memory addresses are function of their respective FHSS signals carrier frequencies.

4. The apparatus of claim 1 further comprising of an array of adjacent-channel-rejecting FHSS baseband signal demodulator circuits each comprised of:
   A FHSS baseband signal demodulator circuit that outputs demodulated data, and
   A circuit that estimates the FHSS baseband signal modulation parameters; and
   A modulator circuit that re-modulates the demodulated data to a re-modulated FHSS signal using the parameters; and
   An adjacent channel interference cancellation circuit that down/up-converts an adjacent channel re-modulated FHSS signal and subtracts it from a FHSS baseband signal to be demodulated.

5. The apparatus of claim 1 further comprising an array of receive-data processing circuits coupled to receive data packets from their respective FHSS baseband signal demodulators, process the received data and store the array of data packets received in memory.

6. The apparatus of claim 1 further comprising a coefficients memory configured to output coefficients to be used to create the imbalance between the FHSS intermediate frequency (IF) I and Q signals, wherein the coefficients memory addresses are function of their respective FHSS signals carrier frequencies.

7. The apparatus of claim 1, wherein a transmit-data processing circuit further delays its output relative to other transmit-data processing circuit outputs.

8. The apparatus of claim 1 further comprising a control circuit that disables a FHSS signal transmission if its carrier frequency is equal to the carrier frequency of another FHSS signal being transmitted.

9. The apparatus of claim 1 further comprising a circuit that offsets a FHSS signal carrier frequency if transmitted simultaneously with an adjacent-channel FHSS signal.

10. A Frequency Hopped Spread Spectrum (FHSS) signals wireless transmitter apparatus comprising:
   An array of transmit-data processing circuits coupled to receive respective transmit data packets from memory, process the transmit data packets and modulate the processed transmit data packets to a an array of FHSS baseband signals, and
   An array of IF up-converters that up-converts the array of FHSS baseband signals to an array of FHSS intermediate frequency (IF) I and Q signals, and
   A I/Q imbalance correction circuit that inputs an array of multiple FHSS IF I and Q signals and outputs an array of imbalanced signals using an array of coefficients, and
   A combiner that combines the array of imbalanced signals to a combined digital signal, and at least one digital to analog converter the converts the combined digital signal to a combined signal, and at least one wide band select filter with bandwidth greater-than at least 5 times the bandwidth of each of the FHSS signals, that filters the combined signal to avoid out-of-band emission and outputs a filtered signal, and
   A radio frequency (RF) synthesizer that generates a synthesized radio frequency, and
   A RF I/Q up-converter that up-converts the filtered signals using the synthesized radio frequency to a signal comprising multiple FHSS signals, and
   An antenna that transmits the signal.

11. The apparatus of claim 10, wherein a FHSS intermediate frequency (IF) I and Q signals imbalance is created using coefficients that are determined as a function of its respective FHSS signal carrier frequency.

12. A wireless transceiver apparatus that transmits and receives multiple FHSS signals at regular time intervals ("frames") according to a preset binary pattern, comprising:
   An antenna that receives a signal comprising multiple FHSS signals, and
   A radio frequency (RF) synthesizer that generates a synthesized radio frequency, and
   A RF downconverter that down-converts the signal using the synthesized radio frequency to an intermediate frequency (IF) signal, and
   at least one wide band select filter with bandwidth greater-than at least 5 times the bandwidth of each of the FHSS signals, that filters the IF signal to reject out-of-band interference and outputs a filtered signal, and
   At least one analog to digital converter that converts the filtered signal to a digitized signal, and
   I/Q imbalance correction circuit that inputs the digitized signal and outputs an array of multiple FHSS intermediate frequency (IF) I and Q signals using an array of coefficients, and
   an array of IF downconverters that down-converts the array of FHSS IF I and Q signals to an array of FHSS zero-IF (ZIF) or low-IF (LIF) signals, and
   an array of channel filters that filters the array of FHSS ZIF or LIF signals and outputs an array of FHSS baseband signals, and
   An array of demodulators that demodulate their respective baseband signals to demodulated data.

13. The wireless transceiver apparatus of claim 12, further comprising: a circuit or processor that controls the transmit power of multiple FHSS devices to equalize their corresponding received FHSS signal levels.

* * * * *